(12) United States Patent
Roh et al.

(10) Patent No.: US 12,006,373 B1
(45) Date of Patent: Jun. 11, 2024

(54) IDENTIFICATION AND EVALUATION OF NOVEL PEPTIDE LIGANDS SPECIFIC TO HUMAN CD3 EPSILON

(71) Applicant: Board of Trustees of the University of Alabama, for and on behalf of the University of Alabama in Huntsville, Huntsville, AL (US)

(72) Inventors: Kyung Ho Roh, Madison, AL (US); Armin Ahmadi, Huntsville, AL (US)

(73) Assignee: Board of Trustees of the University of Alabama, for and on behalf of the University of Alabama in Huntsville, Huntsville, AL (US)

( * ) Notice: Subject to any disclaimer, the term of this patent is extended or adjusted under 35 U.S.C. 154(b) by 0 days.

(21) Appl. No.: 17/349,825

(22) Filed: Jun. 16, 2021

Related U.S. Application Data

(60) Provisional application No. 63/039,751, filed on Jun. 16, 2020.

(51) Int. Cl.
| | | |
|---|---|---|
| *C07K 5/10* | (2006.01) | |
| *C07K 5/103* | (2006.01) | |
| *A61K 38/00* | (2006.01) | |

(52) U.S. Cl.
CPC ............ *C07K 5/1008* (2013.01); *A61K 38/00* (2013.01)

(58) Field of Classification Search
CPC .......... C07K 7/06; C07K 7/08; C07K 5/1008; A61K 38/00
See application file for complete search history.

*Primary Examiner* — Sudhakar Katakam
(74) *Attorney, Agent, or Firm* — Butler Snow LLP; Jon E. Holland

(57) ABSTRACT

The present disclosure is directed to anti-CD3ε peptides, compounds, and methods of using same. A biopanning technique was used to identify several phage clones displaying unique anti-CD3ε peptide sequences. The anti-CD3ε peptide sequences bind to human CD3ε on T cells, allowing the identification, labeling, and delivery of cargo to these T cells. Applications for the disclosed peptides include the labeling of T cells with magnetic particles for MRI detection and targeting of T cells with cargo-laden anti-CD3ε peptides for immunotherapy. Further still, incubation of T cells with anti-CD3ε peptides may result in the activation and increase production of T cells, which may in turn be harvested for applications such as CAR-T therapy.

5 Claims, 13 Drawing Sheets
Specification includes a Sequence Listing.

IDENTIFICATION AND EVALUATION OF NOVEL PEPTIDE LIGANDS SPECIFIC TO HUMAN CD3 EPSILON

RELATED APPLICATION

This application claims priority to U.S. Provisional Patent Application No. 63/039,751 filed on Jun. 16, 2020, titled "Identification and evaluation of novel peptide ligands specific to human CD3," the entire contents of which are incorporated herein.

SEQUENCE LISTING

The instant application contains a Sequence Listing which has been submitted in ASCII format via EFS-Web and is hereby incorporated by reference in its entirety. Said ASCII copy, created on Jun. 10, 2021, is named 02439_0360_SL.txt and is 7,755 bytes in size.

TECHNICAL FIELD

The present disclosure is directed to peptide sequences with binding specificity to human CD3ε.

RELATED ART

As an essential component of the adaptive immune system, T cells play key roles in the implementation of the immune responses against intracellular and extracellular pathogens. The antigen-specific immune response orchestrated by the T cells is initiated by the very specific and sensitive recognition of the antigenic peptide major histocompatibility complex (pMHC) molecules on the antigen presenting cell (APC) surface by the T cell receptors (TCRs) on T cells. The TCR complex is a molecular complex of heterodimeric TCR chains (a pair of α and β for αβ T cells or γ and δ chains for γδ T cells) and CD3 molecules (three dimers of γε, δε, and ζζ or ζη formed by five invariant polypeptide chains, γ, δ, ε, η and ζ) (Birnbaum et al., Proc. Natl. Acad. Sci. 111(49) 17576-81 (2014); Kuhns et al., Immunity 24(2) 133-9 (2006)). While TCR chains are responsible for the direct recognition of antigenic pMHC molecules in ectodomain, the activation signals should be transduced to the cytoplasm via endodomains of CD3 molecules (Dong et al., Nature 573(7775) 546-553 (2019); Wucherpfennig et al., Structural Biology of the T-Cell Receptor: Insights into Receptor Assembly, Ligand Recognition, and Initiation of Signalling, Cold Spring Harb. Perspect. Biol. 2(4) (2010); Nakano et al., J. Biol. Chem. 271(11) 6483-9, (1996)). As such, all CD3 chains are vital for T cell activation and the resulting adaptive immune response. CD3ε, in particular, is expressed as CD3γε and δε dimers (Sommers et al., J. Exp. Med. 192(6) (2000)), and performs an essential role in CD3 core assembly, full TCR complex expression, TCR signaling and T cell development.

Since the first monoclonal antibody (mAb) against CD3 on human T cells was developed, anti-CD3 antibodies coated on a surface of culture plates or on magnetic beads have been utilized as the core elements of many protocols for T cell activation and expansion. Anti-CD3 mAbs have shown their potential to treat autoimmune and inflammatory diseases in preclinical and clinical studies. Numerous commercially available anti-CD3ε mAbs (e.g. clone OKT3 or HIT3a for human) are used for T cell activation assays inducing proliferation and cytokine production.

Despite the use of mAbs in various biomedical applications, their large size (150 k Da for IgG), high cost of manufacturing, and challenges in specific conjugation remain as drawbacks. Thus, various smaller polypeptide structures have been developed as alternative scaffolds of affinity binders. Among them, peptides composed of short amino acid sequences are simple candidates that possess many advantages owing to their small size, ease of synthesis and modification, and great biocompatibility. Short-chain peptides can bind to their target molecules with similar specificity to antibodies but typically with markedly lower affinity. In biology, however, low-affinity interactions between ligand and receptor may be sufficient to induce the intended primary responses depending on the interaction system. The affinities between the TCRs and their cognate agonist pMHCs are relatively low ($K_d$ values in the range of 1-100 μM).

Prior to studies leading to the present disclosure, no previous efforts had been reported to identify and evaluate peptide ligands against CD3ε. The methods and systems described by the present disclosure employ a peptide phage display library and apply an improved biopanning strategy to identify a novel peptide ligand that binds to CD3ε in a specific manner. Using molecular modeling and docking simulation, the structure of the anti-CD3ε peptide is predicted, as well as its binding poses on the surface of CD3. Unlike other protein ligands based on bigger scaffolds, conjugating anti-CD3ε peptide ligands onto various biomaterials platform in a defined orientation is straightforward using commercially available crosslinkers. As a demonstration of the versatility of the present system, sequences, and methods, the disclosed anti-CD3ε peptides were conjugated on the surface of magnetic microbeads and their biological binding efficacies on a human T cell lymphoma line, Jurkat cells, were evaluated. The microbeads coated with the disclosed anti-CD3δ peptides were capable of inducing early T cell activation as measured by calcium flux signaling, without significant upregulation of other activation markers, such as CD25 and CD69, on Jurkat cells. Based on the results, these novel anti-CD3ε peptides have great potential in various applications in T cell biology and immunotherapy.

SUMMARY OF THE DISCLOSURE

The present disclosure is directed to anti-CD3ε peptides, compositions, and methods of using same. In one aspect of the disclosure, there is provided a ligand for binding human cluster of differentiation 3 epsilon (CD3ε), the ligand including an anti-CD3ε peptide that binds specifically to human CD3ε, and optionally including a spacer and attachment group. In some instances, the anti-CD3ε peptide is a peptide selected from the peptides represented by SEQ ID NOS: 1-29. In other instances, the anti-CD3ε peptide is the peptide represented by SEQ ID NO: 11 or SEQ ID NO: 13. In yet other instances, the anti-CD3ε peptide is the peptide represented by SEQ ID NO: 13. In some embodiments, the ligand includes the spacer and attachment group, the ligand having the formula: SEQ ID NO: 30-PEG6-lysine-biotin or SEQ ID NO:31-PEG6-lysine-biotin. In some embodiments, the ligand includes the spacer and attachment group, the ligand having the formula: SEQ ID NO: 32-maleimide-PEG2-biotin. In some embodiments, the ligand is further coupled to a labeling molecule by the attachment group of the ligand, where the labeling molecule is a fluorescent label, enzyme label, chromogenic label, luminescence label, radiation label, magnetic label, metal complex, metal, or colloidal gold. In embodiments where the labeling molecule is a magnetic label and the human CD3ε is present on human T cells, the binding of the ligand to human CD3ε provides identification of the T cells via magnetic resonance imaging (MRI).

In another aspect of the disclosure, a method of providing immunotherapy for the treatment of a disease or condition associated with T cells is disclosed. The method includes the step of administering to a subject an effective amount of a compound including at least one anti-CD3ε peptide or a pharmaceutically acceptable form thereof. In some instances, the disease or condition a cancer or an autoimmune disease. In some instances, the cancer is T cell lymphoma or the autoimmune disease is multiple sclerosis. In the disclosed method, the immunotherapy results from delivery of cargo to healthy or therapeutic T cells using a cargo carrier comprising the at least one anti-CD3ε peptide or pharmaceutically acceptable form thereof either in in-vitro and in-vivo conditions. In some instances, the at least one anti-CD3ε peptide is a peptide selected from the peptides represented by SEQ ID NOS: 1-29. In other instances, the at least one anti-CD3ε peptide is represented by SEQ ID NO: 13.

In yet another aspect of the present disclosure, a method of increasing the production of T cells is disclosed. The method includes the step of applying to T cells an effective amount of a compound including at least one anti-CD3ε peptide or a pharmaceutically acceptable form thereof. The increased T cell production results from the binding of the at least one anti-CD3ε peptide or pharmaceutically acceptable form thereof to human CD3ε present on the T cells. In some instances, the at least one anti-CD3ε peptide is a peptide selected from the peptides represented by SEQ ID NOS: 1-29. In other instances, the at least one anti-CD3ε peptide is represented by SEQ ID NO. 13. The method may further include harvesting the T cells after application of the compound, where the harvested T-cells are used for chimeric antigen receptor T cell (CAR-T) therapy.

A further understanding of the nature and advantages of the present invention will be realized by reference to the remaining portions of the specification and the drawings.

BRIEF DESCRIPTION OF DRAWINGS

The present disclosure can be better understood, by way of example only, with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

Figure 1:
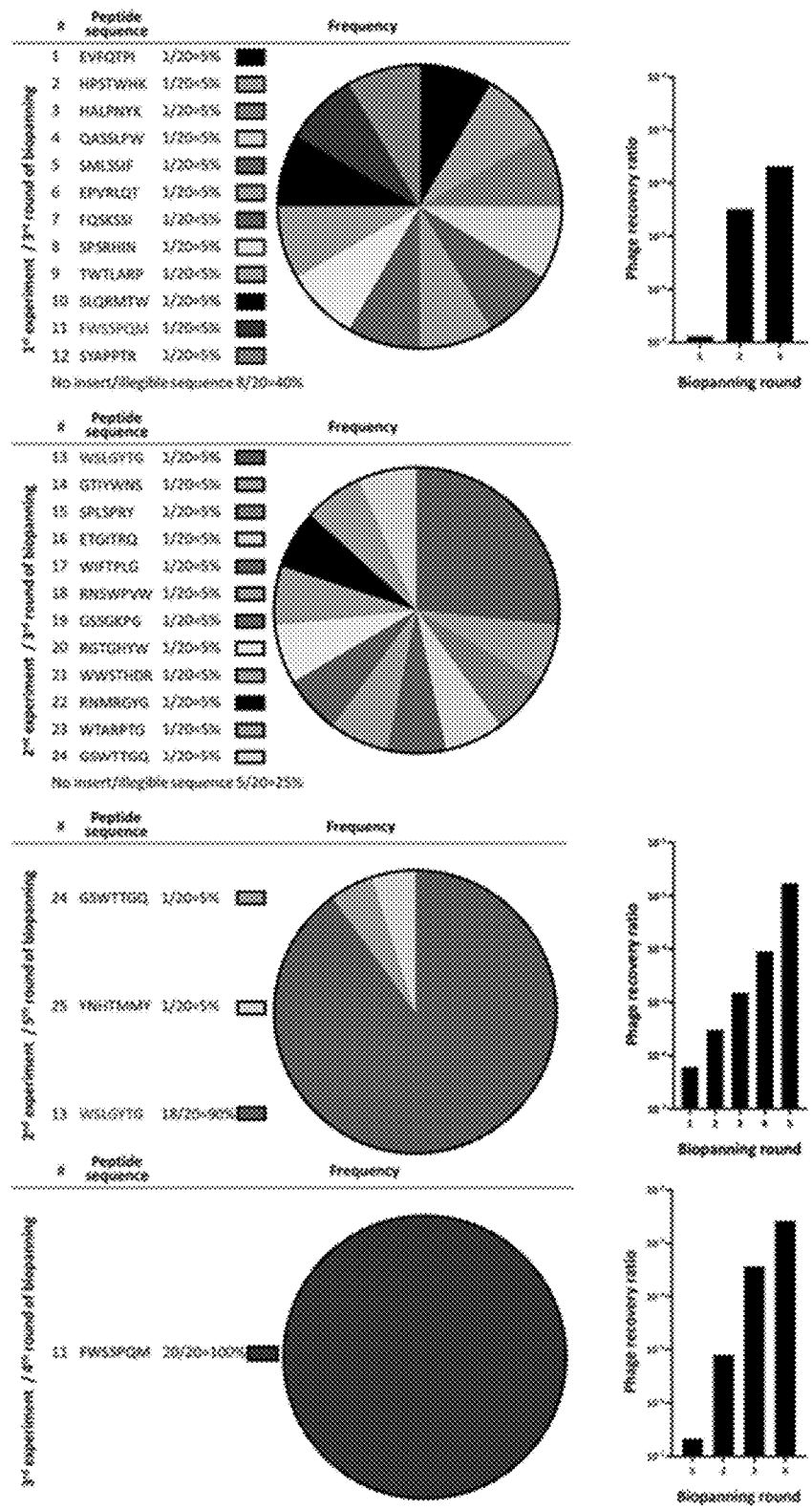
FIG. 1 lists and describes sequences and frequencies of anti-CD3ε peptides of the present disclosure identified in three biopanning experiments. For each biopanning experiment, specific enrichment of recovered phages from each round of selection are shown in the graphs, where phage recovery ratio=output/input phage concentration (PFU/ml).

CD3ε is expressed on T lymphocytes as apart of the T cell receptor (TCR) complex. Together with other CD3 molecules, CD3ε is responsible for activation of T cells via transducing the event of antigen recognition by TCR into intracellular signaling cascades. The present disclosure is generally directed to anti-CD3ε peptide sequences capable of specific binding interactions with human CD3ε. Anti-CD3ε peptides are discovered using biopanning with a peptide phage display library, and evaluated using Jurkat cells, a human T cell line. Upon multiple rounds of biopanning, several phage clones were identified displaying unique anti-CD3ε peptide sequences. One dominant clone displaying 7 amino acid sequence of WSLGYTG, which occupied 90% of tested plaques (18 out of 20) after the 5th round of biopanning, demonstrated superior binding to Jurkat cells in flow cytometry. A tetramer form of the synthesized anti-CD3ε peptide binds to Jurkat cells in a dose-dependent manner but not to a B cell lymphoma line, 2PK3. Molecular modeling and docking simulation confirmed that the selected anti-CD3ε peptide in an energetically stable conformation binds to a pocket of CD3ε that is not hidden by neither CD3δ nor CD3γ. Magnetic microbeads conjugated with the synthesized anti-CD3ε peptides showed a weak but specific association with Jurkat cells and induced the calcium flux, a hallmark indication of proximal T cell receptor signaling. With further investigation, the novel anti-CD3ε peptides and their various multivalent forms have a great potential in applications related to T cell biology and T cell immunotherapy. Further, other discovered or predicted anti-CD3ε peptide sequences may have equal or greater potential for use in applications requiring the specific binding to human CD3ε.

Peptide phage display library is a powerful molecular technique for peptide discovery using a biopanning procedure, in which a library of billions of genetically modified bacteriophages that express randomized unique short peptides as part of their capsid proteins is employed for an affinity selection against the target entities. In brief, this selection or biopanning process is composed of repeated rounds of the following steps: i) incubation of target and the peptide phage library, ii) removal of unbound phage by thorough washing, iii) elution of phage clones that remain bound to the target, and iv) amplification of harvested clones, to eventually find a few of selected peptide ligands against the target. This rapid, simple, cheap, and straightforward technique can typically screen up to $10^7$-$10^9$ unique peptide sequences against a variety of targets including various tissues, cells, proteins, and other organic molecules (Zhang et al., Biotechnol. Lett. 37(11) 2311-20 (2015); Tang et. al., PLoS One 8(1) (2013); McCarthy et al., J. Am. Chem. Soc. 140(19) 6137-45 (2018); Xing et al., Sci. Rep. 8(1) 1-3 (2018)). More specifically, various peptide ligands against cell membrane receptors have been discovered for potential immunological applications. Various binding reagents targeting immune cell markers such as CD19 (Rogers et al., Development of CD19 Binding Reagents for Targeted Nanoparticles (2013)), CD56 (Feng et al., MAbs 8(4) 799-810 (2016)), Ly49A (Tajima et al., Int. Immunol. 16(3) 385-93 (2004)), CD44 (Zhang et al., Biotechnol. Lett. 37(11) 2311-20 (2015)), CCR5 (Wang et al., Biosci. Biotechnol. Biochem. 70(9) 2035-41 (2006)), CD20 (Goracci et al., Molecules 25(4) 1-28 (2020)), and PDL1 (Gurung et al., Biomaterials 247 119984 (2020)) have been selected using biopanning of phage display libraries.

The terms "anti-CD3ε peptide", "anti-CD3ε peptides", "peptide of the disclosure", "peptides of the disclosure", "disclosed peptide" or "disclosed peptides" refer to any one or combination peptides with binding specificity to human CD3ε. For example, anti-CD3ε peptides include those represented by SEQ ID NOS 1-29, in modified form similar to those represented by SEQ ID NOS 30-32, or a variant thereof having at least 75% identity to peptides or molecules represented by SEQ ID NOS: 1-32.

The term "Cluster of Differentiation 3 Epsilon (CD3ε)" refers to the protein encoded by the human CD3ε gene, which together with CD3-γ, -δ and -ζ, and the T-cell receptor α/β and γ/δ heterodimers, forms the T-cell receptor-CD3 complex. CD3ε is recognized in T-cell development and the adaptive immune response.

The term "compound(s) of the disclosure" as used herein means a peptide of the disclosure, or a pharmaceutically acceptable form thereof. In certain aspects, a compound of the disclosure is any one or combination of peptides represented by SEQ ID NOS: 1-29 or in modified form similar to those represented by SEQ ID NOS 30-32 as described herein, or a variant thereof having at least 75% identity to peptides or molecules represented by SEQ ID NOS: 1-32.

The term "pharmaceutically acceptable" refers to a compound that is compatible with the other ingredients of a composition and not deleterious to the subject receiving the compound or composition. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

The term "pharmaceutical composition" refers to a mixture of one or more of the compounds of the disclosure, with other components, such as, but not limited to, pharmaceutically acceptable carriers and/or excipients. The purpose of a pharmaceutical composition is to facilitate administration of a compound of disclosure.

The term "protein," "peptide," "polypeptides" and "oligopeptides" refer to chains of amino acids (typically L-amino acids) whose alpha carbons are linked through peptide bonds formed by a condensation reaction between the carboxyl group of the alpha carbon of one amino acid and the amino group of the alpha carbon of another amino acid. Typically, the amino acids making up a protein are numbered in order, starting at the amino terminal residue and increasing in the direction toward the carboxy terminal residue of the protein.

The terms "treatment" or "treating" as used herein means an approach for obtaining beneficial or desired results, including clinical results. Beneficial or desired clinical results in the context of the present disclosure include, but are not limited to, prevention or reduction of an immune disorder or condition, or of any condition involving T cells. "Treatment" or "treating" involves alleviation or amelioration of one or more symptoms or conditions, a diminution of extent of disease, a stabilized (i.e., not worsening) state of disease, and/or delaying or slowing of disease progression, amelioration or palliation of the disease state and remission (whether partial or total). "Treatment" or "treating" can also mean prolonging survival as compared to expected survival if not receiving treatment.

Compounds of the Disclosure

In one aspect of the present disclosure, there is presented synthetic anti-CD3ε peptides, which bind human CD3ε. In certain aspects, anti-CD3ε peptide 1 is set forth in SEQ ID NO: 1, anti-CD3ε peptide 2 is set forth in SEQ ID NO: 2, anti-CD3ε peptide 3 is set forth in SEQ ID NO: 3, anti-CD3ε peptide 4 is set forth in SEQ ID NO: 4, anti-CD3ε peptide 5 is set forth in SEQ ID NO: 5, anti-CD3ε peptide 6 is set forth in SEQ ID NO: 6, anti-CD3ε peptide 7 is set forth in SEQ ID NO: 7, anti-CD3ε peptide 8 is set forth in SEQ ID NO: 8, anti-CD3ε peptide 9 is set forth in SEQ ID NO: 9, anti-CD3ε peptide 10 is set forth in SEQ ID NO: 10, anti-CD3ε peptide 11 is set forth in SEQ ID NO: 11, anti-CD3ε peptide 12 is set forth in SEQ ID NO: 12, anti-CD3ε peptide 13 is set forth in SEQ ID NO: 13, anti-CD3ε peptide 14 is set forth in SEQ ID NO: 14, anti-CD3ε peptide 15 is set forth in SEQ ID NO: 15, anti-CD3ε peptide 16 is set forth in SEQ ID NO: 16, anti-CD3ε peptide 17 is set forth in SEQ ID NO: 17, anti-CD3ε peptide 18 is set forth in SEQ ID NO: 18, anti-CD3ε peptide 19 is set forth in SEQ ID NO: 19, anti-CD3ε peptide 20 is set forth in SEQ ID NO: 20, anti-CD3ε peptide 21 is set forth in SEQ ID NO: 21, anti-CD3ε peptide 22 is set forth in SEQ ID NO: 22, anti-CD3ε peptide 23 is set forth in SEQ ID NO: 23, anti-CD3ε peptide 24 is set forth in SEQ ID NO: 24, anti-CD3ε peptide 25 is set forth in SEQ ID NO: 25, anti-CD3ε peptide 26 is set forth in SEQ ID NO: 26, anti-CD3ε peptide 27 is set forth in SEQ ID NO: 27, anti-CD3ε peptide 28 is set forth in SEQ ID NO: 28, and anti-CD3ε peptide 29 is set forth in SEQ ID NO: 29. In alternative aspects, anti-CD3ε peptide 1 has a sequence that has 50% or greater, 60% or greater, 70% or greater, 80% or greater, 90% or greater, 95% or greater, or 99% or greater sequence identity to SEQ ID NO: 1, preferably 90% or greater or 95% or greater sequence identity. In alternative aspects, anti-CD3ε peptide 2 has a sequence that has 50% or greater, 60% or greater, 70% or greater, 80% or greater, 90% or greater, 95% or greater, or 99% or greater sequence identity to SEQ ID NO: 2, preferably 90% or greater or 95% or greater sequence identity. In alternative aspects, anti-CD3ε peptide 3 has a sequence that has 50% or greater, 60% or greater, 70% or greater, 80% or greater, 90% or greater, 95% or greater, or 99% or greater sequence identity to SEQ ID NO: 3, preferably 90% or greater or 95% or greater sequence identity. In alternative aspects, anti-CD3ε peptide 4 has a sequence that has 50% or greater, 60% or greater, 70% or greater, 80% or greater, 90% or greater, 95% or greater, or 99% or greater sequence identity to SEQ ID NO: 4, preferably 90% or greater or 95% or greater sequence identity. In alternative aspects, anti-CD3ε peptide 5 has a sequence that has 50% or greater, 60% or greater, 70% or greater, 80% or greater, 90% or greater, 95% or greater, or 99% or greater sequence identity to SEQ ID NO: 5, preferably 90% or greater or 95% or greater sequence identity. In alternative aspects, anti-CD3ε peptide 6 has a sequence that has 50% or greater, 60% or greater, 70% or greater, 80% or greater, 90% or greater, 95% or greater, or 99% or greater sequence identity to SEQ ID NO: 6, preferably 90% or greater or 95% or greater sequence identity. In alternative aspects, anti-CD3ε peptide 7 has a sequence that has 50% or greater, 60% or greater, 70% or greater, 80% or greater, 90% or greater, 95% or greater, or 99% or greater sequence identity to SEQ ID NO: 7, preferably 90% or greater or 95% or greater sequence identity. In alternative aspects, anti-CD3ε peptide 8 has a sequence that has 50% or greater, 60% or greater, 70% or greater, 80% or greater, 90% or greater, 95% or greater, or 99% or greater sequence identity to SEQ ID NO: 8, preferably 90% or greater or 95% or greater sequence identity. In alternative aspects, anti-CD3ε peptide 9 has a sequence that has 50% or greater, 60% or greater, 70% or greater, 80% or greater, 90% or greater, 95% or greater, or 99% or greater sequence identity to SEQ ID NO: 9, preferably 90% or greater or 95% or greater sequence identity. In alternative aspects, anti-CD3ε peptide 10 has a sequence that has 50% or greater, 60% or greater, 70% or greater, 80% or greater, 90% or greater, 95% or greater, or 99% or greater sequence identity to SEQ ID NO: 10, preferably 90% or greater or 95% or greater sequence identity. In alternative aspects, anti-CD3ε peptide 11 has a sequence that has 50% or greater, 60% or greater, 70% or greater, 80% or greater, 90% or greater, 95% or greater, or 99% or greater sequence identity to SEQ ID NO: 11, preferably 90% or greater or 95% or greater sequence identity. In alternative aspects, anti-CD3ε peptide 12 has a sequence that has 50% or greater, 60% or greater, 70% or greater, 80% or greater, 90% or greater, 95% or greater, or 99% or greater sequence identity to SEQ ID NO: 12, preferably 90% or greater or 95% or greater sequence identity. In alternative aspects, anti-CD3ε peptide 13 has a sequence that has 50% or greater, 60% or greater, 70% or greater, 80% or greater, 90% or greater, 95% or greater, or 99% or greater sequence identity to SEQ ID NO: 13, preferably 90% or greater or 95% or greater sequence identity. In alternative aspects, anti-CD3ε peptide 14 has a sequence that has 50% or greater, 60% or greater, 70% or greater, 80% or greater, 90% or greater, 95% or greater, or 99% or greater sequence identity to SEQ ID NO: 14, preferably 90% or greater or 95% or greater sequence identity. In alternative aspects, anti-CD3ε peptide 15 has a sequence that has 50% or greater, 60% or greater, 70% or greater, 80% or greater, 90% or greater, 95% or greater, or 99% or greater sequence identity to SEQ ID NO: 15, preferably 90% or greater or 95% or greater sequence identity. In alternative aspects, anti-CD3ε peptide 16 has a sequence that has 50% or greater, 60% or greater, 70% or greater, 80% or greater, 90% or greater, 95% or greater, or 99% or greater sequence identity to SEQ ID NO: 16, preferably 90% or greater or 95% or greater sequence identity. In alternative aspects, anti-CD3ε peptide 17 has a sequence that has 50% or greater, 60% or greater, 70% or greater, 80% or greater, 90% or greater, 95% or greater, or 99% or greater sequence identity to SEQ ID NO: 17, preferably 90% or greater or 95% or greater sequence identity. In alternative aspects, anti-CD3ε peptide 18 has a sequence that has 50% or greater, 60% or greater, 70% or greater, 80% or greater, 90% or greater, 95% or greater, or 99% or greater sequence identity to SEQ ID NO: 18, preferably 90% or greater or 95% or greater sequence identity. In alternative aspects, anti-CD3ε peptide 19 has a sequence that has 50% or greater, 60% or greater, 70% or greater, 80% or greater, 90% or greater, 95% or greater, or 99% or greater sequence identity to SEQ ID NO: 19, preferably 90% or greater or 95% or greater sequence identity. In alternative aspects, anti-CD3ε peptide 20 has a sequence that has 50% or greater, 60% or greater, 70% or greater, 80% or greater, 90% or greater, 95% or greater, or 99% or greater sequence identity to SEQ ID NO: 20, preferably 90% or greater or 95% or greater sequence identity. In alternative aspects, anti-CD3ε peptide 21 has a sequence that has 50% or greater, 60% or greater, 70% or greater, 80% or greater, 90% or greater, 95% or greater, or 99% or greater sequence identity to SEQ ID NO: 21, preferably 90% or greater or 95% or greater sequence identity. In alternative aspects, anti-CD3ε peptide 22 has a sequence that has 50% or greater, 60% or greater, 70% or greater, 80% or greater, 90% or greater, 95% or greater, or 99% or greater sequence identity to SEQ ID NO: 22, preferably 90% or greater or 95% or greater sequence identity. In alternative aspects, anti-CD3ε peptide 23 has a sequence that has 50% or greater, 60% or greater, 70% or greater, 80% or greater, 90% or greater, 95% or greater, or 99% or greater sequence identity to SEQ ID NO: 23, preferably 90% or greater or 95% or greater sequence identity. In alternative aspects, anti-CD3ε peptide 24 has a sequence that has 50% or greater, 60% or greater, 70% or greater, 80% or greater, 90% or greater, 95% or greater, or 99% or greater sequence identity to SEQ ID NO: 24, preferably 90% or greater or 95% or greater sequence identity. In alternative aspects, anti-CD3ε peptide 25 has a sequence that has 50% or greater, 60% or greater, 70% or greater, 80% or greater, 90% or greater, 95% or greater, or 99% or greater sequence identity to SEQ ID NO: 25, preferably 90% or greater or 95% or greater sequence identity. In alternative aspects, anti-CD3ε peptide 26 has a sequence that has 50% or greater, 60% or greater, 70% or greater, 80% or greater, 90% or greater, 95% or greater, or 99% or greater sequence identity to SEQ ID NO: 26, preferably 90% or greater or 95% or greater sequence identity. In alternative aspects, anti-CD3ε peptide 27 has a sequence that has 50% or greater, 60% or greater, 70% or greater, 80% or greater, 90% or greater, 95% or greater, or 99% or greater sequence identity to SEQ ID NO: 27, preferably 90% or greater or 95% or greater sequence identity. In alternative aspects, anti-CD3ε peptide 28 has a sequence that has 50% or greater, 60% or greater, 70% or greater, 80% or greater, 90% or greater, 95% or greater, or 99% or greater sequence identity to SEQ ID NO: 28, preferably 90% or greater or 95% or greater sequence identity. In alternative aspects, anti-CD3ε peptide 29 has a sequence that has 50% or greater, 60% or greater, 70% or greater, 80% or greater, 90% or greater, 95% or greater, or 99% or greater sequence identity to SEQ ID NO: 29, preferably 90% or greater or 95% or greater sequence identity.

The peptides of the disclosure can be produced using various techniques known in the art. For recombinant production of peptides of the disclosure including a heterologous amino acid sequence, nucleic acid encoding a peptide of the disclosure and a desired heterologous amino acid sequence can be synthesized and inserted into one or more vectors for further cloning and/or expression in host cells. Peptides of the disclosure lacking a heterologous sequence may be produced in the same manner, with the exception that the cDNA does not encode the heterologous amino acid sequence. In some embodiments, peptides of the disclosure having one or more amino acid substitutions, insertions or deletions are generated by site-directed mutagenesis or other methods known in the art. Such nucleic acid may be readily isolated and sequenced using conventional procedures. Expression vectors comprising a peptides of the disclosure can be transfected into the host cells or stably expressed in the host cells. Suitable host cells for cloning or expression of the peptides of the disclosure include prokaryotic or eukaryotic cells. Expression of the peptides of the disclosure can be achieved used yeast, insect, or mammalian expression systems. The expressed anti-CD3ε peptides can be purified using methods known in the art. For example, a peptide of the disclosure may be purified by affinity chromatography using an appropriate monoclonal antibody or using the optional sequence tag disclosed herein. The purified anti-CD3ε peptides can be verified by using SDS page or Western Blot analysis, as is known in the art. Or as an alternative route, the peptides can be directly synthesized by solid-phase peptide synthesis.

Anti-CD3ε Peptide Variants

The peptides of the disclosure also include peptide variants having one or more substitutions, insertions and/or deletions relative to a reference amino acid sequence. For example, a peptide of the disclosure may include one or more amino acid substitutions relative to a reference amino acid or sequence. For example, a variant peptide may include a non-conservative and/or conservative amino acid substitution relative to a reference peptide. Conservative amino acid substitutions are those substitutions that are predicted to interfere least with the properties of the reference peptide. Conservative amino acid substitutions generally maintain one or more of: (a) the structure of the peptide backbone in the area of the substitution, for example, as a beta sheet or alpha helical conformation, (b) the charge or hydrophobicity of the molecule at the site of the substitution, and/or (c) the bulk of the side chain. Logically, a non-conservative amino acid substitution will not generally maintain one or more of: (a) the structure of the peptide backbone in the area of the substitution, for example, as a beta sheet or alpha helical conformation, (b) the charge or hydrophobicity of the molecule at the site of the substitution, and/or (c) the bulk of the side chain.

The following Table 1 provides a list of exemplary conservative and highly conservative amino acid substitutions.

TABLE 1

| Original Amino Acid | Conservative Amino Acid Substitution |
|---|---|
| Glycine (G) | A |
| Alanine (A) | S, G, T |
| Serine (S) | T, A, N |
| Threonine (T) | S, A, V, N |
| Cysteine (C) | A |
| Proline (P) | A |
| Methionine (M) | L, I, V |
| Valine (V) | I, L, M |
| Leucine (L) | M, I, V, F |
| Isoleucine (I) | V, L, M, F |
| Phenylalanine (F) | W, L |
| Tyrosine (T) | F, W |
| Tryptophan (W) | F |
| Asparagine (N) | Q |
| Glutamine (Q) | N |
| Aspartic Acid (D) | E |
| Glutamic Acid (E) | D |
| Histidine (H) | R, K |
| Lysine (K) | R, H |
| Arginine (R) | K, H |

For example, a conservative amino acid substitution may involve a substitution of a native amino acid residue with a nonnative residue such that there is little or no effect on the polarity, steric bulk, charge, hydrophobicity and/or hydrophilicity of the amino acid residue at that position. Conservative amino acid substitutions also encompass non-naturally occurring amino acid residues which are typically incorporated by chemical peptide synthesis rather than by synthesis in biological systems. These include peptidomimetics, and other reversed or inverted forms of amino acid moieties. It will be appreciated by those of skill in the art that polypeptide described herein may be chemically synthesized as well as produced by recombinant means.

In making an amino acid substitution as described herein, the hydropathic index of an amino acid may be considered. Each amino acid has been assigned a hydropathic index on the basis of their hydrophobicity and charge characteristics. Hydropathic index values are resented by: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (Kyte et al., J. Mol. Biol., 157:105-131, 1982). It is known that certain amino acids may be substituted for other amino acids having a similar hydropathic index or score and still retain a similar biological activity. In one embodiment, making changes based upon the hydropathic index, the substitution of amino acids whose hydropathic indices are within +/−1; in an alternate embodiment, the hydropathic indices are within +/−0.5; in yet another alternate embodiment, the hydropathic indices are within +/−0.25.

In making an amino acid substitution as described herein, the hydrophilicity may also be considered. In certain embodiments, the greatest local average hydrophilicity of a polypeptide as governed by the hydrophilicity of its adjacent amino acids, correlates with a biological property of the protein. The following hydrophilic index values have been assigned to amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In one embodiment, in making changes based upon similar hydrophilicity values, the substitution of amino acids whose hydrophilicity values are within +/−1; in an alternate embodiment, the hydrophilicity values are within +/−0.5; in yet another alternate embodiment, the hydrophilicity values are within +/−0.25.

A skilled artisan will be able to determine suitable substitutions, insertions and deletions, including combinations thereof, of an anti-CD3ε peptide as set forth in any of SEQ ID NOS: 1-29 using techniques known in the art. Further, a skilled artisan will be able to determine suitable substitutions, insertions and deletions, including combinations thereof, of a modified anti-CD3ε peptide as set forth in any of SEQ ID NOS: 30-32 using techniques known in the art. For identifying suitable areas of a peptide that may be changed without destroying activity, one skilled in the art may target areas not believed to be important for activity. For example, when homologous peptides with similar activities from the same species or from other species are known, one skilled in the art may compare the amino acid sequence of a peptide described herein to such homologous peptides. With such a comparison, one can identify residues and portions of the molecules that are conserved among similar peptides. It will be appreciated that changes in areas of a peptide described herein that are not conserved relative to such homologous peptide would be less likely to adversely affect the biological activity and/or structure of a peptide described herein. One skilled in the art would also know that, even in relatively conserved regions, one may substitute chemically similar amino acids for the naturally occurring residues while retaining activity (for example, conservative amino acid substitutions). Therefore, even areas that may be important for biological activity or for structure may be subject to such amino acid substitutions without destroying the biological activity or without adversely affecting the peptide structure. With regard to deletions, a peptide variant may be generated by deleting one or more amino acids from the n-terminal portion and/or the c-terminal portion of the amino acid sequence.

The deletions, insertions, and substitutions can be selected, as would be known to one of ordinary skill in the art, to generate a desired peptide variants. For example, it is not expected that deletions, insertions, and substitutions in a non-functional region of a peptide would alter activity. Likewise conservative amino acid substitutions and/or substitution of amino acids with similar hydrophilic and/or hydropathic index values is expected to be tolerated in a conserved region and a polypeptide activity may be conserved with such substitutions.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

Methods of Treatment and Use

The peptides and compounds of the disclosure are useful for a variety of purposes. The peptides and compounds of the disclosure may be used in methods to identify, label, bind, or deliver cargo to T cells having CD3ε. Further, the peptides and compounds of the disclosure may be used to produce or increase production of T cells for a variety of downstream applications.

In a first aspect, the present disclosure provides a method for identifying or labeling T cells having CD3ε, such as for magnetic resonance imaging (MRI) or fluorescence imaging of T cells in immunotherapy applications. In such applications, anti-CD3ε peptides include additional components, such as spacers, attachment molecules, sequences, or regions, and/or labels. Spacers include repeating or minimally-interacting amino acids added to provide space between the functional anti-CD3ε peptide sequence and an attached sequence or molecule. Examples of such spacers include, but are not limited to the spacer sequence GGGS or GGGSC. Anti-CD3ε peptides 11 and 13 are combined with the spacer GGGS as FWSSPQMGGGS (SEQ ID NO: 30) and WSLGYTGGGGS (SEQ ID NO: 31), respectively. Further, anti-CD3ε peptide 13 is combined with the spacer GGGSC as WSLGYTGGGGSC (SEQ ID NO: 32). Spacers may also include chemical structures that separate the functional anti-CD3ε peptide from labels or attached molecules. Spacers have variable lengths and may be hydrophobic or hydrophilic. Examples of spacing sequences include, but are not limited to aminohexanoic acid, beta-alanine, 4-aminobutyric acid, (2-aminoethoxy) acetic acid, 5-aminovaleric acid, polyethylene glycol (PEG)-2, PEG-3, PEG-4, PEG-5, PEG-6, and Ttds (Trioxatridecan-succinamic acid). Attachment molecules allow the synthetic peptide to be attached to a region of another structure, surface, or molecule. Attachment molecules include, but are not limited to biotin, streptavidin, maleimide, thiol, cysteine, lysine, N-hydroxysuccinimide (NHS), gold, copper, and avidin.

In one embodiment of the present disclosure, an anti-CD3ε peptide or composition can be fused with one or more detectable labels. Labels may be compounds which can be detected in chemical, physical or biological responses, or compounds which generate signals directly or indirectly in the responses. Labeling and detecting after then can be performed according to the known method in the art (For example, Sambrook, J., and Russel, D. W. (2001); and Lottspeich, P., and Zorbas H. (1998) Bioanalytik, Spektrum Akademischer Verlag, Heidelberg/Berlin, Germany). Labels comprise fluorescent labels, enzyme labels, chromogenic labels, luminescence labels, radiation labels, magnetic labels, hapten, biotin, metal complex, metal and colloidal gold, but not limited to those. All forms of these labels are well known in this field of work, they can be commercially obtained from various suppliers.

In some embodiments of the foregoing methods, an application step comprises administering an effective amount of a compound of the disclosure, or a composition, comprising a compound of the disclosure and a carrier, to a population of T cells or suspected T cells. The population of T cells or suspected T cells is in vitro in some instances, or in vivo in other instances. Application of the anti-CD3ε peptides, or a compound containing the anti-CD3ε peptides, may occur on a clinical setting, a laboratory setting, a production or manufacturing setting, or other locations. In embodiments of the foregoing methods, the disclosed compound is selected from the anti-CD3ε peptides set forth in any of SEQ ID NOS: 1-29. In preferred embodiments of the foregoing methods, the disclosed compound is the anti-CD3ε peptide set forth in SEQ ID NO: 11 or SEQ ID NO: 13. In highly preferred embodiments of the foregoing methods, the disclosed compound is the anti-CD3ε peptide set forth in SEQ ID NO: 13.

In one aspect of the present disclosure, a cargo can be directly combined with the anti-CD3ε peptide. In such embodiments, cargo may be attached as described herein regarding the attachment of labels, such as through the use of spacers and/or attachment molecules. In another embodiment of the present disclosure, a cargo can be combined to the anti-CD3ε peptide via various types of bonds such as covalent or non-covalent bonds. A cargo, for example, can be combined to the N-terminal or C-terminal of the anti-CD3ε peptide in one embodiment of the present invention. For example, a cargo can be bonded to the anti-CD3ε peptide by disulfide bonds or covalent bonds. The covalent bonds are the bonds that a cargo can be bonded to α-amine of N-terminal glutamate, or amine of C-terminal Lysine residues. Also, an anti-CD3ε peptide and a cargo can be combined via a non-covalent bond, which can have either a peptide or a cargo can encapsulate the other as a capsule form. In another embodiment of the present disclosure, an anti-CD3ε peptide can be combined with a cargo via a linker. For example, an anti-CD3ε peptide can be combined with a cargo by binding a cargo to a linker after introducing a linker such as biotin to the anti-CD3ε peptide and coupling the biotin to avidin or streptavidin on the cargo. Cargo may be used to provide treatment for a condition, such as treatment for T cell lymphoma, multiple sclerosis, or other immunotherapy, autoimmune disease, or cancer applications.

In some embodiments, the disclosure provides for the use of a pharmaceutical composition and/or medicaments comprising a compound of the disclosure in any of the methods described herein. In some embodiments, the methods of treatment include administering to a subject an amount of a disclosed compound produced by methods of the present disclosure. Administration is done alone or as part of a pharmaceutical composition, and may be undertaken by any route, including, but not limited to, intravenously, intraperitoneally, parenterally, intramuscularly, orally, rectally, intranasally (nose drops), by inhalation via the pulmonary system, topically, or transdermally. In any of the foregoing methods of treatment, subjects treated may be further treated with one or more additional active agents know for the treatment of a disease or condition, or which may increase the effectiveness of a disclosed compound. Additional active agents described herein or pharmaceutically acceptable forms thereof can be administered together in a single composition with a disclosed compound, or in separate compositions in any order, including simultaneous administration, as well as temporally spaced on the order of minutes, days, or weeks apart. Methods can also include more than a single administration of the one or more additional active agents and/or a disclosed compound or pharmaceutically acceptable forms thereof. Administration can be undertaken using the same or different routes and concurrently or sequentially. In any of the foregoing methods, the subject is a mammal. In any of the foregoing methods, the subject is a human.

In some embodiments of the foregoing methods, the administering step comprises administering an effective amount of a compound of the disclosure, or a composition, such as a pharmaceutical composition, comprising a compound of the disclosure and a pharmaceutically acceptable carrier, to a subject. In embodiments of the foregoing methods, the disclosed compound is selected from the anti-CD3ε peptides set forth in any of SEQ ID NOS: 1-29. In preferred embodiments of the foregoing methods, the disclosed compound is the anti-CD3ε peptide set forth in SEQ ID NO: 11 or SEQ ID NO: 13. In highly preferred embodiments of the foregoing methods, the disclosed compound is the anti-CD3ε peptide set forth in SEQ ID NO: 13.

In yet another aspect of the present disclosure, anti-CD3ε peptides and compounds may be used to produce or increase production of T cells through activation of T cells through CD3ε binding. In such embodiments, anti-CD3ε peptides for activation described herein include similar components to those describes for attachment of labels, such as spacers and/or attachment molecules. As shown in greater detail in the following examples, prior art CD3ε activation binding molecules, such as anti-CD3ε antibodies, have a generally higher affinity for CD3ε than the disclosed peptides. This higher affinity for anti-CD3ε antibodies leads to tighter binding to T cells relative to the disclosed peptides, which, in some instances, results in induced upregulation of activation markers and a reduction in T cell proliferation, potentially due to the activation-induced apoptosis. The presently disclosed peptides bind specifically, but with a generally lower affinity than anti-CD3ε antibodies, to cells displaying human CD3ε. This binding behavior allows the presently disclosed peptides to activate and increase T cell production without or with minimal activation-induced apoptosis. T cells produced using the disclosed peptides or compounds may be harvested for downstream applications, such as chimeric antigen receptor T cell (CAR-T) therapy.

In some embodiments of the foregoing methods, an application step comprises administering an effective amount of an anti-CD3ε peptide or compound of the disclosure, or a composition, comprising a compound of the disclosure and a carrier, to a population of T cells or suspected T cells. The population of T cells or suspected T cells is in vitro in some instances, or in vivo in other instances. Application of the anti-CD3ε peptides, or a compound containing the anti-CD3ε peptides, may occur on a clinical setting, a laboratory setting, a production or manufacturing setting, or other locations. In embodiments of the foregoing methods, the disclosed compound is selected from the anti-CD3ε peptides set forth in any of SEQ ID NOS: 1-29. In preferred embodiments of the foregoing methods, the disclosed compound is the anti-CD3ε peptide set forth in SEQ ID NO: 11 or SEQ ID NO: 13. In highly preferred embodiments of the foregoing methods, the disclosed compound is the anti-CD3ε peptide set forth in SEQ ID NO: 13.

Dosage and Administration

In accordance with some aspects of the present disclosure, the compounds of the disclosure are administered to the subject (or are contacted with cells of the subject) in an effective amount. In certain embodiments, the effective amount of a compound of the disclosure is that which is effective, for example, to treat an immune disorder or disease or to identify cells related to a condition. In certain embodiments, the effective amount of a compound of the disclosure is that which is effective, for example, to identify cells related to a condition and to diagnose a subject with that condition when a sufficient amount of the identified cells are present.

In certain embodiments, only one dose of a compound of the disclosure is administered during a course of treatment and no further doses are administered. Therefore, in the methods described herein the methods may comprise the administration of a single dose of an effective amount of a compound of the disclosure during the entire course of treatment. In certain embodiments, the single dose contain an effective amount of a compound of the disclosure.

In certain embodiments, more than one dose of a compound of the disclosure is administered during a course of treatment. Therefore, in the methods described herein, the methods may comprise the administration of multiple doses during the course of treatment. In certain embodiments, a dose is delivered at least 1 time per day (i.e., 1 to 3 times) during the course of treatment. In certain embodiments, a dose is not administered every day during the course of treatment (for example, a dose is be administered at least 1 timer per day every other day, every third day, or every week during the course of treatment). Furthermore, the amount of a compound of the disclosure in each dose need not be the same as discussed above. In certain embodiments, of the foregoing, one or more doses, preferably all of the doses, contain an effective amount of a compound of the disclosure.

The pharmaceutical compositions disclosed may comprise one or more compound of the present disclosure, alone or in combination with additional active agents, in combination with a pharmaceutically acceptable carrier. Examples of such carriers and methods of formulation may be found in Remington: The Science and Practice of Pharmacy (20$^{th}$ Ed., Lippincott, Williams & Wilkins, Daniel Limmer, editor). Such pharmaceutical compositions may be used in the manufacture of a medicament for use in the methods of treatment and prevention described herein. The compounds of the disclosure are useful in both free form and in the form of pharmaceutically acceptable salts.

The pharmaceutically acceptable carriers described herein, including, but not limited to, vehicles, adjuvants, excipients, or diluents, are well-known to those who are skilled in the art. Pharmaceutically acceptable excipients are also well-known to those who are skilled in the art. The choice of excipient will be determined in part by the particular compound(s), as well as by the particular method used to administer the composition. Accordingly, there is a wide variety of suitable formulations of the pharmaceutical composition of the present invention. The following methods and excipients are merely exemplary and are in no way limiting. Suitable carriers and excipients include solvents such as water, alcohol, and propylene glycol, solid absorbants and diluents, surface active agents, suspending agent, tableting binders, lubricants, flavors, and coloring agents. The pharmaceutically acceptable carriers can include polymers and polymer matrices. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. Typically, the pharmaceutically acceptable carrier is chemically inert to the active agents in the composition and has no detrimental side effects or toxicity under the conditions of use. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

Surfactants such as, for example, detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sulfate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula N+R'R''R'''R''''Y—, in which the R radicals are identical or different optionally hydroxylated hydrocarbon radicals and Y— is an anion of a strong acid, such as halide, sulfate and sulfonate anions; cetyltrimethylammonium bromide is one of the cationic surfactants which can be used, amine salts of formula N+R'R''R''', in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine.

In these pharmaceutical compositions, the compound(s) of the present disclosure will ordinarily be present in an amount of about 0.1-95% weight based on the total weight of the composition. Multiple dosage forms may be administered as part of a single treatment.

In one embodiment, the compounds of the present disclosure are administered in therapeutically effective amount, whether alone or as a part of a pharmaceutical composition. The therapeutically effective amount and the dosage administered will, of course, vary depending upon known factors, such as the pharmacodynamic characteristics of the particular agent and its mode and route of administration, the age, health and weight of the recipient; the severity and stage of the disease state or condition; the kind of concurrent treatment; the frequency of treatment; and the effect desired.

The total amount of the compound administered will also be determined by the route, timing and frequency of administration as well as the existence, nature, and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

Kits

The present disclosure also provides a kit for use in the methods described herein, the kit comprising a compound of the disclosure, or a pharmaceutically acceptable form thereof, and at least one of the following: (i) at least one other therapeutic agent; (ii) packaging material; (iii) instructions for administering the compound of the disclosure, or pharmaceutically acceptable form thereof and the other therapeutic agent or agents to a subject to treat a subject.

In one embodiment, the present disclosure provides a kit comprising an anti-CD3ε peptide as set forth in any of SEQ ID NOS: 1-29, a pharmaceutically acceptable form thereof, or a modified anti-CD3ε peptide as set forth in any of SEQ ID NOS: 30-32, and at least one of the following: (i) at least one other therapeutic agent; (ii) packaging material; (iii) instructions for administering the compound of the disclosure, or pharmaceutically acceptable form thereof and the other therapeutic agent or agents to a subject to treat a subject.

In one embodiment, the present disclosure provides a kit comprising more than one of the anti-CD3ε peptides set forth in SEQ ID NOS: 1-29, a pharmaceutically acceptable forms thereof, or a modified anti-CD3ε peptide as set forth in any of SEQ ID NOS: 30-32, and at least one of the following: (i) at least one other therapeutic agent; (ii) packaging material; (iii) instructions for administering the compound of the disclosure, or pharmaceutically acceptable form thereof and the other therapeutic agent or agents to a subject to treat a subject.

In one embodiment, the present disclosure provides a kit comprising the anti-CD3ε peptide as set forth in SEQ ID NO: 11 or the anti-CD3ε peptide as set forth in SEQ ID NO: 13, a pharmaceutically acceptable forms thereof, or a modified anti-CD3ε peptide as set forth in any of SEQ ID NOS: 30-32, and at least one of the following: (i) at least one other therapeutic agent; (ii) packaging material; (iii) instructions for administering the compound of the disclosure, or pharmaceutically acceptable form thereof and the other therapeutic agent or agents to a subject to treat a subject.

In one embodiment, the present disclosure provides a kit comprising the anti-CD3ε peptide as set forth in SEQ ID NO: 13, or a pharmaceutically acceptable form thereof, and at least one of the following: (i) at least one other therapeutic agent; (ii) packaging material; (iii) instructions for administering the compound of the disclosure, or pharmaceutically acceptable form thereof and the other therapeutic agent or agents to a subject to treat a subject.

In one embodiment of the kits disclosed, the subject is a human. In another embodiment of the kits disclosed, the compound of the disclosure has an anti-CD3ε peptide sequence including, but not limited to all or any of the sequences set forth in any of SEQ ID NOS: 1-32.

All patent applications, patents, and printed publications which are cited to be incorporated by reference are incorporated by reference in their entireties unless otherwise noted, except for any definitions, subject matter disclaimers or disavowals, and except to the extent that the incorporated material is inconsistent with the express disclosure herein, in which case the language in this disclosure controls.

Example 1

1.1 Materials and Cell Cultures: The Ph.D.-7 phage display peptide library kit including *E. coli* strain ER2738 was purchased from New England BioLabs (NEB, MA, USA). The library is consists of approximately $10^9$ unique sequences and includes random heptapeptides fused to N-terminus of minor coat protein (pIII) of M13 phage. −96 gIII sequencing primer (5'-CCCTCATAGT-TAGCGTAACG-3') was ordered from Integrated DNA Technologies (IDTDNA, IA, USA). A recombinant CD3ε protein with Fc-tag was purchased from Sino Biological (PA, USA). Anti-M13 Major Coat Protein (RL-ph1) antibody was purchased from Santa Cruz Biotechnology (TX, USA). Paraformaldehyde fixation buffer was obtained from eBioscience (CA, USA). Biotin anti-human CD3ε (OKT3) antibody, PE anti-human CD25 (BC96) and Alexa Fluor 488 anti-human CD69 (FN50) antibodies were purchased from Biolegend (CA, USA). Pierce protein A/G magnetic beads, Alexa Fluor 488 streptavidin, Zeba spin desalting columns, EZ-Link maleimide-PEG2-biotin, M280 streptavidin Dynabeads, Fluo-4 AM and pluronic F-127 were all purchased from Thermo Fisher Scientific (MA, USA).

Human Jurkat T cells (E6-1) and 2PK3 mouse B lymphoma cells were acquired from American Type Culture Collection (ATCC, USA) and maintained in culture with complete growth media, RPMI-1640 or DMEM supplemented with 10% FBS, respectively, at 37° C. under 5% $CO_2$. Cells were collected from the culture flask and stained with trypan blue to confirm >90% viability before each experiment.

1.2 Biopanning: Screening of the Ph.D.-7 phage display peptide library on human recombinant CD3ε protein as the target protein was carried out according to the manufacturer's protocol with modifications. Briefly, 50 µl of a 50% aqueous suspension of Pierce protein A/G magnetic beads was washed with 1 ml of TBST washing buffer (tris-buffered saline with 0.1% tween) on a magnetic separator and blocked in blocking buffer (0.1 M $NaHCO_3$ (pH 8.6) with 0.5% (w/v) BSA) for 1 h at 4° C. on a rotator. Two picomoles of target protein was mixed with $10^{11}$ pfu (plaque-forming unit) of the phage library in 200 µl of TBST buffer and incubated for 15 minutes at room temperature on a rotator and then incubated with pre-washed and pre-blocked magnetic beads for 15 minutes at room temperature on a rotator. After the microbeads were washed vigorously for 15 times with 1 ml TBST, the bound phage was eluted by 1 ml of glycine buffer (0.2 M Glycine-HCl (pH 2.2)+0.1% (w/v) BSA) and neutralized by addition of 150 µl of 1 M Tris-HCl (pH 9.1). The harvested phages were amplified by infecting *E. coli* (ER2738) cells and precipitated using PEG8000/NaCl solution. After each round, a negative selection was performed by incubating the harvested phage clones from the previous round with the empty protein A/G magnetic beads in TBST buffer for 20 minutes at room temperature on a rotator. Only the unbound phages in this negative selection were used for the next rounds of panning. After the third and the fifth round of biopanning, the resulting phage clones tittered on LB/IPTG/Xgal plates, and 20 out of 100 blue plaques were randomly picked for sequencing.

1.3 DNA Sequencing of Phage Clones: After the third and fifth round of biopanning, the ssDNA of selected phage clones was harvested following the standard protocol (NEB). Briefly, selected each blue plaque was added into 500 µl of *E. coli* (ER2738) culture ($OD_{650}$ of 0.5) and amplified for approximately 5 hours until it reached $OD_{650}$ of 3. After spinning down the cells using microcentrifugation at 14,000 rpm for 20 min, phages were precipitated using 200 µl of 20% PEG/2.5 M NaCl for 20 minutes at room temperature from each supernatant. Following spinning down the precipitates by centrifugation at 14,000 rpm for 10 minutes at 4° C., the pellets were suspended in 100 µl of Iodide Buffer (10 mM Tris-HCl, 1 mM EDTA, 4 M sodium iodide, pH of 8) to isolate the single-stranded phage DNA. The DNA was precipitated by adding 250 µl of ethanol and incubating for 20 minutes at room temperature. The centrifuged pellet was washed again by 0.5 ml of 70% ethanol (−20° C.), dried under vacuum, and resuspended in 30 µl of TE buffer (10 mM Tris-HCl, 1 mM EDTA, pH of 8). The purified DNA of each clone was sequenced by Sanger sequencing (UAB Genomics Core Laboratories) using the −96 gIII primer and analyzed using Geneious Prime 2019 software suite.

1.4 Affinity Screening of Phage Clones: All phage clones harvested from the blue plaques were amplified, tittered, and their concentrations (PFU/ml) were measured. Jurkat cells were washed once with FACS buffer (PBS supplemented with 0.1% BSA and 2 mM EDTA) and plated into 96 microplates with phage clones ($10^{10}$ PFU phages with $10^5$ cells per each well) and incubated for 30 minutes on ice. After incubation, the cells were washed with FACS buffer and incubated with anti-M13 Major Coat Protein antibody diluted in FACS buffer (1:100) for 30 min on ice. Then, samples were washed and resuspended in FACS buffer to be analyzed by flow cytometry. For a comparison of phage clone 1 and two random clones, the same procedure was employed except the Jurkat cells were pre-fixed using 4% paraformaldehyde before incubation with the phage clones.

1.5 Molecular Docking: Three-dimensional (3D) structure models of anti-CD3ε peptide clones 11 and 13 were generated using the PEP-FOLD3 peptide structure prediction server (Thevenet et al., Nucleic Acids Res. 40 (W1) 288-293 (2012); Shen et al., J. Chem. Theory Comput. 10(10), 4745-4758 (2014)), based on the Hidden Markov model (PEP-FOLD Peptide Structure Prediction Server, bioserv.rpbs.univ-paris-diderot.fr/services/PEP-FOLD3/). Each anti-CD3ε peptide structure was docked on the energy-minimized CD3ε structure using the protein docking facility in the program MOE version 2019 (Chemical Computing Group, Montreal, Canada). The crystal structure of human CD3ε that was previously reported was employed (Arnett et al., Proc. Natl. Acad. Sci. 101(46), 16268-16273 (2004); Dong et al., Nature 573(7775), 546-552 (2019)) (PDB ID: 1XIW, in which CD3ε and CD3δ in complex with anti-CD3ε single-chain antibody fragment clone UCHT1, and PDB ID: 6JXR, in which a complex of CD3ε, δ, γ, and ζ chains in association with αβ TCR). The coordinates for the 7 amino acid sequences omitted from the ectodomain of CD3ε at C-terminus were added to the model using the MOE homology modeling facility. For each 3D peptide model, 100 different binding poses were generated. All 500 docked complexes were further refined by energy minimization run and sorted by their binding energy calculated by from the Molecular Mechanics Poisson-Boltzmann Surface Area (MMIPBSA) method (Genheden et al., Expert Opin. Drug Discov. 10(5), 449-461 (2015)). The interface of interaction was also analyzed using MOE. All illustrations were generated using PyMOL (The PyMOL Molecular Graphics System, Version 2.0. Schrödinger, LLC), MOE, or LigPlot+ (Laskowski et al., J. Chem. Inf. Model. 51(10), 2778-2786 (2011)).

1.6 Preparation of Peptide Tetramer: Peptide synthesis: The anti-CD3ε peptide 13 (WSLGYTG) containing Gly-Gly-Gly-Ser spacer sequence (same as the linker on the coat protein pIII of the M13 phage in Ph.D-7 phage library) followed by PEG6, lysine and biotin, at the C-terminus (WSLGYTGGGGS-PEG6-K-Biotin) was synthesized by GenScript (NJ, USA) using Fmoc solid-phase peptide synthesis chemistry (>98% purity).

Tetramer formation: The anti-CD3ε peptide tetramers were prepared by incubating biotinylated anti-CD3ε peptide with Alexa Fluor 488 streptavidin (10:1 molar ratio) for 30 minutes at room temperature, and an excess of anti-CD3ε peptides were washed using Zeba spin desalting columns (7 kDa MWCO).

1.7 Binding and Activation Assays using Peptide Tetramers: Human Jurkat cells (clone E6-1) and 2PK3 mouse B lymphoma cells were collected from the culture flask, washed with FACS buffer, and plated into V-bottom 96 microplates and incubated with indicated doses of anti-CD3ε peptide tetramers or naked streptavidin-AF488 (negative control for binding assay) or tetramer of anti-human CD3 antibody (OKT3) (positive control for activation assay). For the binding assay, the microplate containing the samples was incubated for 30 minutes on ice, and the cells were washed with and resuspended in FACS buffer to be analyzed by flow cytometry. For the activation assay, the samples were incubated for 12 hours within the incubator (37° C. and 5% $CO_2$) before analyzed by flow cytometry.

1.8 Peptide Beads: The anti-CD3ε peptide 13 with Gly-Gly-Gly-Ser spacer followed by Cys at the C-terminus (WSLGYTGGGGSC) was synthesized by GenScript (NJ, USA) with Fmoc solid-phase chemistry. The synthesized anti-CD3ε peptide was biotinylated by incubating a mixture of 0.2% (w/v) peptide solution in DMF with 20-fold molar excess of EZ-Link maleimide-PEG2-biotin (Pierce) in the presence of 50 mM triethanolamine for overnight at room temperature on a rotator. The biotinylated anti-CD3ε peptide (WSLGYTGGGGSC-PEG2-BIOTIN) was purified from excess of reagents and byproducts using Zeba spin desalting columns (7 kDa MWCO). M280 streptavidin Dynabeads (2.8 µm in diameter) were coated with biotinylated anti-CD3ε peptide in a saturating density (200 pmol of biotinylated anti-CD3ε peptides per 1 mg of Dynabeads). For positive control, M280 beads were coated with biotin anti-human CD3 (OKT3) antibody.

1.9 Monitoring Interactions Between Peptide Beads and Jurkat Cells: Dynabeads coated with indicated reagents were incubated with $10^5$ Jurkat or 2PK3 cells (5 beads:1 cell) in 96 well plate for 48 h at 37° C. in a standard $CO_2$ incubator. Each well was examined at 1, 6, 12, and 24 hours under the optical microscopy. After 24 hours of incubation, cells were harvested and analyzed by flow cytometry to examine the expression of activation markers. After 48 hours of incubation, the number of live cells was counted using a hemocytometer.

1.10 Flow Cytometry: Jurkat cells were incubated with the indicated reagents (phages, peptide tetramer, and/or antibodies) for 30 minutes on ice, washed with FACS buffer, and resuspended in 300-500 µl FACS buffer. Each sample was analyzed by using Attune NxT flow cytometer (Invitrongen) equipped with two lasers at 488 nm and 647 nm. The results were analyzed using FlowJo software.

1.11 Monitoring Calcium Signalling: Jurkat cells were collected from culture flask, washed and resuspended in fresh complete RPMI media. After confirming >90% viability, cells were incubated with 10 µM Fluo-4 AM and 0.05% (v/v) Pluronic F-127 for 1 hour at room temperature. After washing twice with PBS, cells were resuspended in pre-warmed RPMI media containing 1% (v/v) prolong live antifade reagent and 1 mM extra $CaCl_2$) and kept in a dark condition for 20 min at room temperature. $0.5 \times 10^6$ cells were mixed with beads coated with indicated reagents (5 beads:1 cell) and loaded onto a well of 24-well plate that was kept on top of the onstage incubator (37° C. and 5% $CO_2$) of EVOS FL Auto microscope. After waiting 10 minutes for cell and beads to settle down, time-laps videos of green fluorescence and brightfield channels were acquired for 2 hours at every 10-second interval. The time-lapse video was then analyzed using ImageJ software with FIJI plugin (Schindelin et al., Nat. Methods 9(7), 676-682 (2012)).

1.12 Statistical Analysis: Statistical analysis for multi-group comparison was performed by one-way analysis of variance (ANOVA) method using GraphPad Prism. When appropriate, all data from replicates were expressed as the mean±standard deviation. From student t-test, $p<0.05$ was considered statistically significant.

2.1 Specific Enrichment of Phages Bound on CD3ε: Phage clones that bind specifically to the recombinant human CD3ε protein were identified through biopanning experiments using 7-mer peptide phage library. As shown in FIG. 1, after each round of panning, the phage recovery ratio was measured and it showed an exponential increase up to the $5^{th}$ round, which indicates that the phage clones capable of specifically binding to CD3ε were significantly enriched at every round of biopanning. Twenty out of about 100 plaques (colonies from tittered Xgal-IPTG plates) were randomly selected and the ssDNA from each clone was purified after $3^{rd}$ rounds. From three separate experiments, 25 unique anti-CD3ε peptide sequences were identified in FIG. 1. The corresponding frequency of each sequence clearly demonstrated dominant enrichments of phage clones 11 and 13, displaying anti-CD3ε peptides FWSSPQM and WSLGYTG, respectively.

Figure 2:
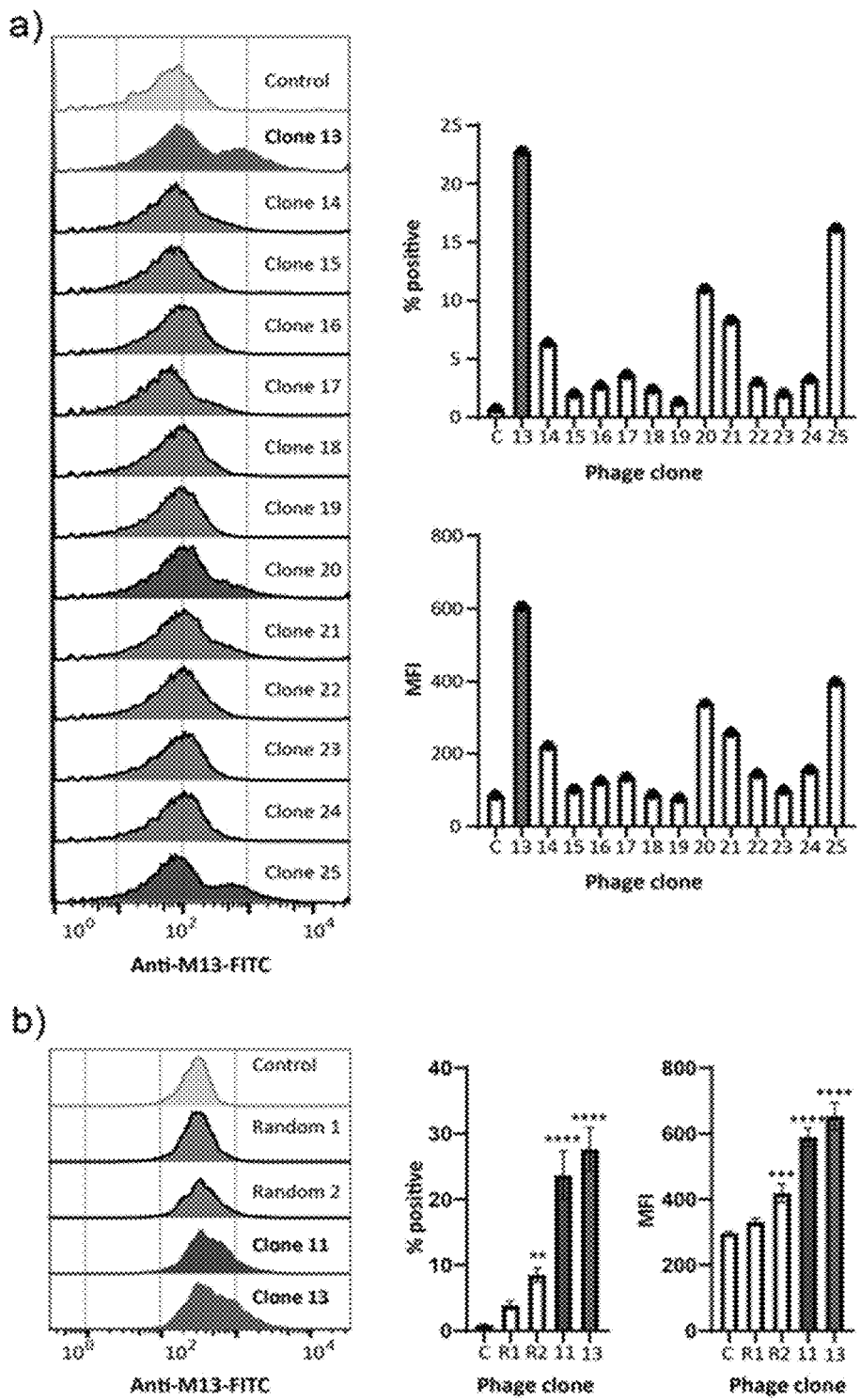
FIG. 2 displays affinity screening of a) all phage clones and b) phage clones 11, 13, and two random clones against Jurkat cells expressing CD3ε to obtain sequences of the present disclosure. The results are presented as means±SD, n=3, ****P<0.0001.

2.2 Specific Binding of Phage Clones onto Jurkat T Cells: The relative binding behaviors of all 13 phage clones identified from the $2^{nd}$ biopanning experiment were first examined using Jurkat T cells expressing CD3ε. For comparative binding, the dose of each phage clone per Jurkat cell was kept identical ($10^{10}$ PFU per 105 Jurkat cells). In FIG. 2, the amount of phage bound to Jurkat cells for each clone was quantified by staining the phage using anti-M13 antibody followed by flow cytometry analysis. Phage clone 13 showed the best binding behavior both in terms of the size of positive Jurkat cell population and the MFI values. Similarly, the binding behaviors of phage clones 11 and 13 were compared with two completely random phage clones onto Jurkat cells in FIG. 2. In order to make sure the observed binding is not a result of other interactions between live Jurkat cells and bacteriophages, fixed Jurkat cells were used as binding partners. Again, phage clones 11 and 13 were superior to the random controls in binding to the fixed Jurkat cells. Altogether, these results indicate that the peptide of phage clones selected from biopanning against the recombinant protein CD3ε can specifically bind to the physiological CD3ε molecules expressed on the plasma membrane of Jurkat cells as part of TCR-CD3 molecular complexes, where the ectodomain of CD3ε is paired with CD3γ or δ chains in a side-by-side way as CD3γε or CD3δε heterodimers. Therefore, the data suggests that the phage clones, especially phage clones 11 and 13, can bind to the exposed part of physiological polypeptide CD3ε that is not hidden by either CD3γ or δ chains.

Figure 3:
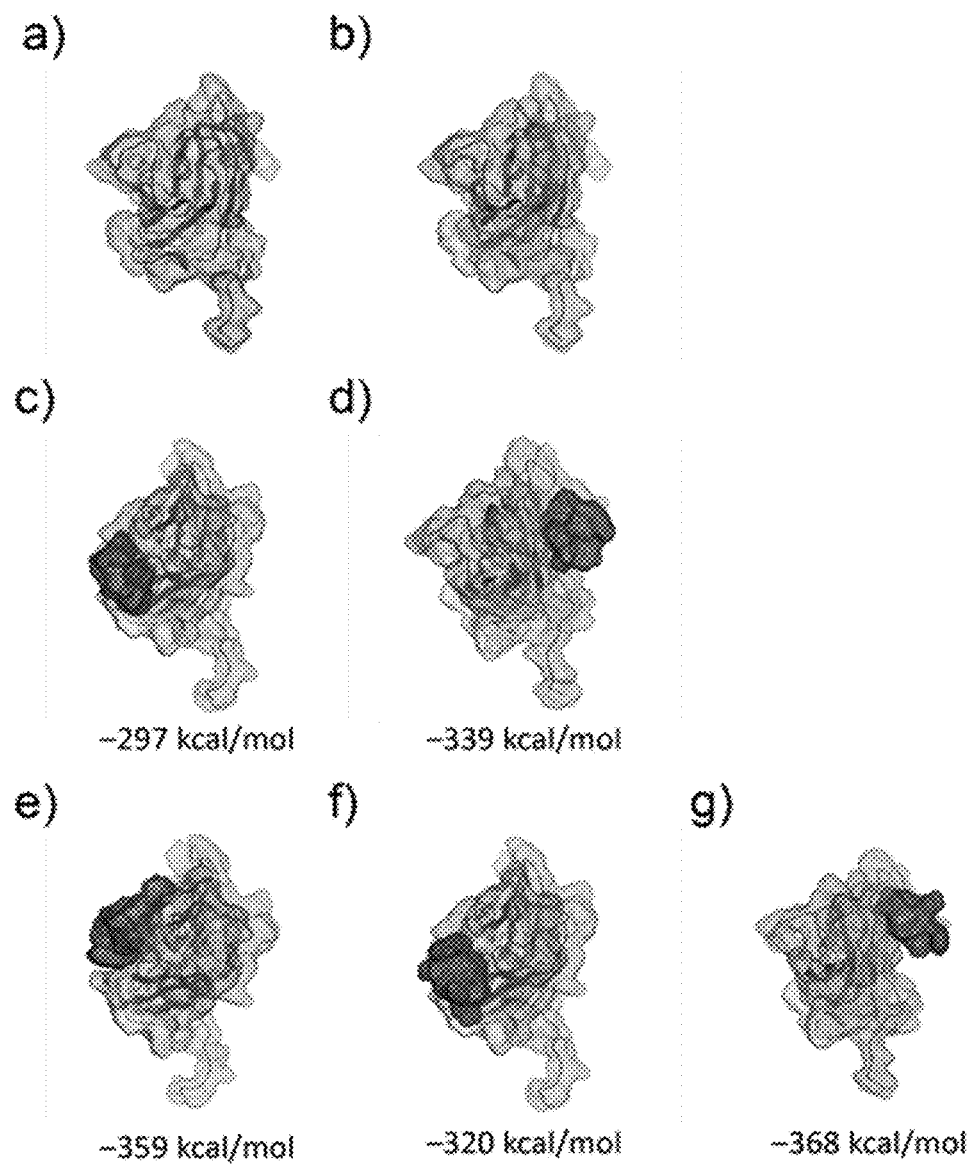
FIG. 3 displays schematics showing the most favorable binding poses of anti-CD3ε peptides 13 and 11, and their binding energy levels (MMPBSA) predicted by molecular docking. a) The 3-dimensional structure of human CD3ε chain is shown. b) The interface between CD3ε and CD3δ or CD3γ chains is overlaid in lightened grey on the right side of the schematic (PDB ID: 6JXR). The binding site of anti-CD3ε single-chain antibody fragment clone UCHT1 (PDB ID: 1XIW) is overlaid in grey on the left side of the schematic. The best binding poses of anti-CD3ε peptide 13 (c, d) and anti-CD3ε peptide 11 (e-g) are shown in dark grey on the "exposed" (c, e, f) or "unexposed" (d, g) sites of CD3ε.
Figure 8:
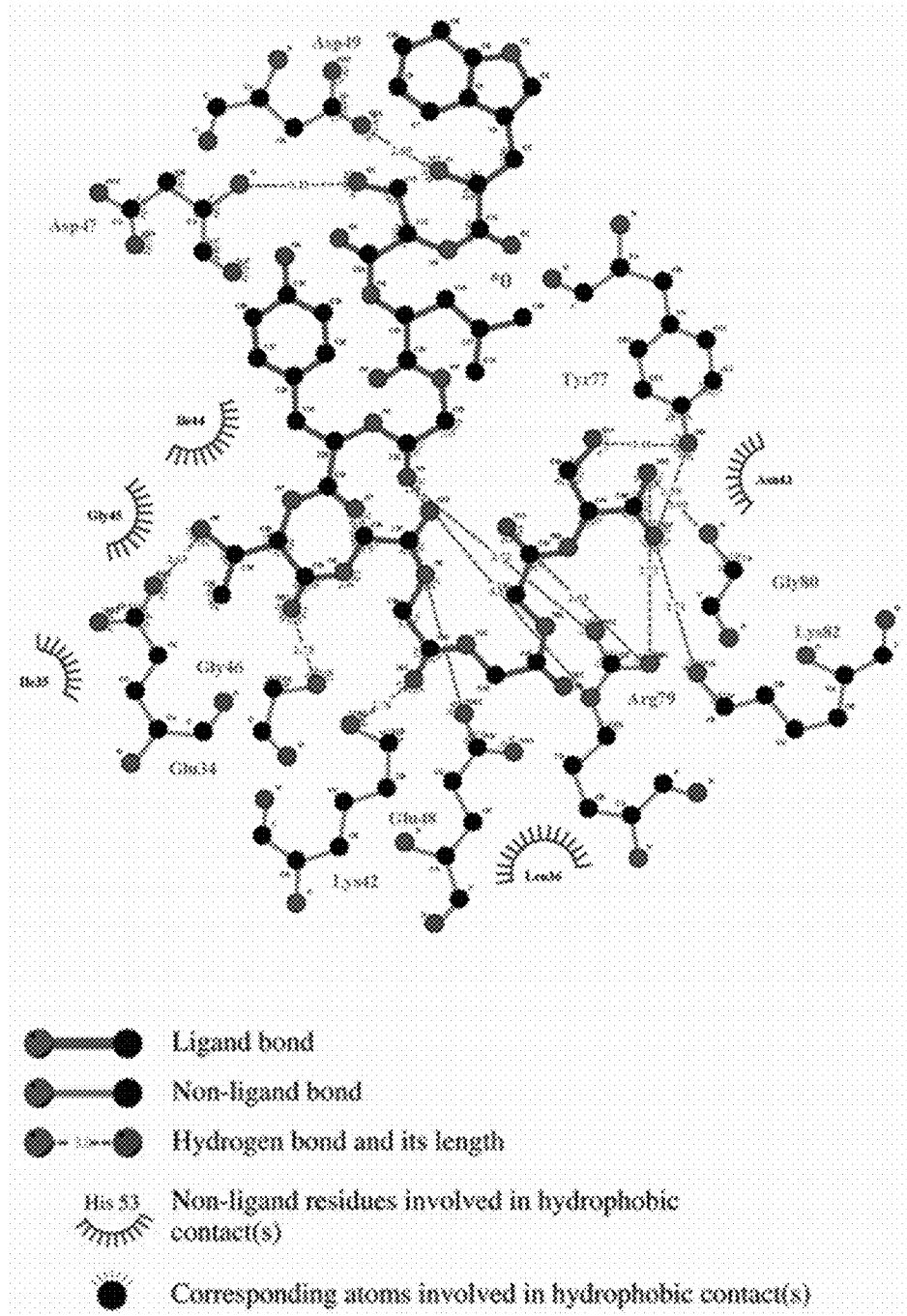
FIG. 8 is a schematic showing a two-dimensional illustration of interactions between anti-CD3ε peptide 13 and the exposed epitope of CD3ε.

2.3 Prediction of Favorable Binding Poses by Molecular Docking: In order to better understand the potential binding sites as well as the nature of the binding, the energetically favorable binding poses of anti-CD3ε peptide 13 (WSLGYTG) and 11 (FWSSPQM) on CD3ε were examined using molecular docking simulations. The most energetically favorable peptide poses (dark grey in FIG. 3) on CD3ε (light grey in FIG. 3) were identified by calculating each binding energy (kcal/mol) based on Molecular Mechanics Poisson-Boltzmann Surface Area (MM/PBSA) method. In fact, the most energetically favorable pose overlaps with the interface between CD3ε and CD3δ or CD3γ chains, which are herein called the "unexposed" side of CD3ε (FIG. 3, panels d and g). However, other binding poses were also identified on the "exposed" epitope of CD3ε, i.e. on the side of CD3ε that are not interfaced with any other CD3 chains, at a comparable binding energy level, as shown in FIG. 3, panels c, e, and f. It appears that all energetically favorable binding poses on both the "exposed" and the "unexposed" epitopes of CD3ε may have contributed to these peptides' dominant enrichment behaviors during the biopanning experiment. However, the actual binding affinities of anti-CD3ε peptides 11 and 13 to the physiological CD3ε on T lymphocytes should only originate from the binding to the "exposed" epitope. This explains well the fact that the binding of phage clones 11 and 13 were superior to other clones but not as dominant as it appeared in the biopanning enrichment data. The interactions between anti-CD3ε peptide 13 and the "exposed" epitope of CD3ε are mainly driven by 14 hydrogen bonds as well as 5 hydrophobic contacts, as shown in FIG. 8.

The binding sites of anti-CD3ε peptides 11 and 13 were also compared with the binding epitope of UCHT1 single-chain antibody fragment against CD3ε (PDB ID: 1XIW). The UCHT1-binding epitope slightly overlaps with the binding epitope of peptides on the "exposed" side of CD3ε, as shown in FIG. 3 panel c.

2.4 Further Analysis of Peptide Sequences by Molecular Docking: All of the anti-CD3ε peptide sequences identified from biopanning experiments using molecular docking on CD3ε protein were examined and compared the most favorable binding poses of each anti-CD3ε peptide using PEP-FOLD3 peptide structure prediction server to predict most stable forms of the peptides and pepATTRACT blind rigid peptide-protein docking server (Schindler et al., Structure, 23(8), 1507-1515(2015); de Vries et al., Nucleic Acids Res. 45(W1), W361-W364 (2017)) which run the docking on the cloud and return 50 models with each model being the lowest-energy structure of a docking cluster based in their "ATTRACT force field energy".

Although the calculated energy levels may not be directly leveraged to predict the exact binding affinities, the most favorable poses of peptides on exposed and unexposed sites of CD3ε can be estimated and thus the sequences that have greater potential to bind to the physiological CD3ε are selected. Table 2 shows that some anti-CD3ε peptide sequences (SYAPPTR, GTIYWNS, WIFTPLG, RNSWPVW, RNMRGYG, YNHTMMY, among others) have potential to specifically bind to the physiological CD3ε with a similar or even greater affinities than the anti-CD3ε peptides 11 or 13.

The following Table 2 provides all anti-CD3ε peptide sequences identified from the biopanning experiments along with their corresponding ATTRACT energy levels.

TABLE 2

| Anti-CD3ε peptide # | Sequence | Max energy | Energy exposed site | Energy unexposed site |
|---|---|---|---|---|
| 1 (SEQ ID NO: 1) | EVFQTPI | −10.99 | | |
| 2 (SEQ ID NO: 2) | HPSTWHK | −14.27 | −12.60 | −14.27 |
| 3 (SEQ ID NO: 3) | HALPNYK | −15.06 | −13.84 | −15.06 |
| 4 (SEQ ID NO: 4) | QASSLPW | −12.95 | | |
| 5 (SEQ ID NO: 5) | SMLSSIF | −13.52 | −10.48 | −13.52 |
| 6 (SEQ ID NO: 6) | EPVRLQT | −12.33 | | |
| 7 (SEQ ID NO: 7) | FQSKSSI | −12.61 | | |
| 8 (SEQ ID NO: 8) | SPSRHIN | −12.97 | | |
| 9 (SEQ ID NO: 9) | TWTLARP | −13.41 | −12.29 | −13.41 |
| 10 (SEQ ID NO: 10) | SLQRMTW | −13.61 | −13.35 | −13.61 |
| 11 (SEQ ID NO: 11) | FWSSPQM | −14.29 | −13.20 | −14.29 |
| 12 (SEQ ID NO: 12) | SYAPPTR | −14.69 | −14.69 | −13.95 |
| 13 (SEQ ID NO: 13) | WSLGYTG | −14.57 | −14.2 | −14.57 |
| 14 (SEQ ID NO: 14) | GTIYWNS | −15.17 | −15.17 | −12.95 |
| 15 (SEQ ID NO: 15) | SPLSPRY | −12.24 | | |
| 16 (SEQ ID NO: 16) | ETGITRQ | −11.17 | | |
| 17 (SEQ ID NO: 17) | WIFTPLG | −14.44 | −14.44 | −13.83 |
| 18 (SEQ ID NO: 18) | RNSWPVW | −14.92 | −14.92 | −14.84 |
| 19 (SEQ ID NO: 19) | GSSGKPG | −12.13 | | |
| 20 (SEQ ID NO: 20) | RGTGHYW | −15.22 | −15.22 | −14.49 |
| 21 (SEQ ID NO: 21) | WWSTHDR | −15.56 | −13.99 | −15.56 |
| 22 (SEQ ID NO: 22) | RNMRGYG | −15.86 | −14.58 | −15.86 |
| 23 (SEQ ID NO: 23) | WTARPTG | −14.21 | −12.1 | −14.21 |
| 24 (SEQ ID NO: 24) | GSWTTGQ | −15.22 | −11.93 | −15.22 |
| 25 (SEQ ID NO: 25) | YNHTMMY | −15.68 | −14.38 | −15.68 |

Looking carefully the 25 sequences from biopanning experiments, it was found that some combination of amino acids in anti-CD3ε, peptide sequences are repeated multiple times among all sequences (Table 3).

The following Table 3 provides the frequencies of the two-letter sequences that repeatedly appear on the 25 anti-CD3ε, peptide sequences identified from the biopanning experiments.

TABLE 3

| Amino acid combinations | Number of anti-CD3ε peptides with this combination |
|---|---|
| S S | 5 |
| T G | 5 |
| S P | 4 |
| W S | 3 |
| W T | 3 |
| T W | 3 |

Based on these repeated combinations and their position in the structure of the sequence, a list of possible anti-CD3ε peptide sequences with these limitations was randomly generated. Checking the most favorable docking poses of these generated peptides, four more sequences were identified to add, as shown in Table 4.

The following Table 4 provides the anti-CD3ε peptide sequences that were identified from a combinatorial generation of 7-mer sequences using the limitations described in the text and their corresponding ATTRACT energy levels.

TABLE 4

| Sequence | Max energy | Energy exposed site | Energy unexposed site |
|---|---|---|---|
| WWSSPTG (SEQ ID NO: 26) | −16.33 | −14.12 | −16.33 |
| WMSSPTG (SEQ ID NO: 27) | −16.56 | −13.19 | −16.56 |
| WISSPTG (SEQ ID NO: 28) | −13.71 | −13.18 | −13.71 |
| TWSSPTG (SEQ ID NO: 29) | −13.17 | −13.17 | −13.17 |

Figure 4:
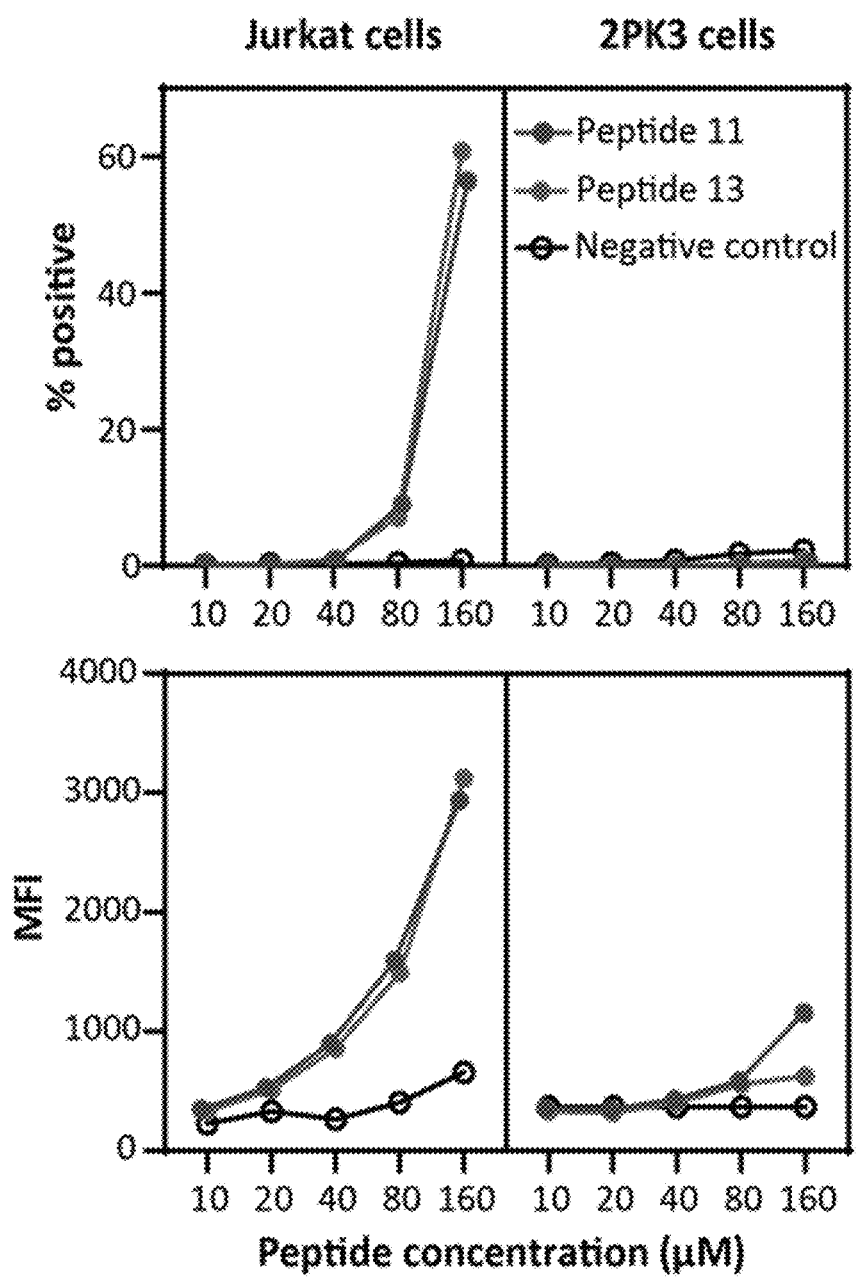
FIG. 4 displays graphical representations of the selective binding of tetramers of anti-CD3ε peptides 11 and 13 toward Jurkat and 2PK3 cells as a function of anti-CD3ε peptide concentration.

2.5 Selective Affinity of Peptide Tetramers: To investigate the selective binding of synthesized anti-CD3ε peptide 11 and 13 against CD3ε expressed on Jurkat cells, the anti-CD3ε peptides with C-terminal biotin (FWSSPQMGGGS [SEQ ID NO: 30]-PEG6-K-biotin or WSLGYTGGGGS [SEQ ID NO: 31]-PEG6-K-biotin) were prepared as shown by example in FIG. 9 panel a. Varying concentrations of tetramer of peptides based on streptavidin-biotin interaction were incubated with Jurkat T cells or 2PK3 B cells. 2PK3 cells are a mouse B lymphoma cell line, so it shares common features of lymphoblast with Jurkat T cells but lacks the expression of TCR-CD3 complexes. Peptide tetramers showed incremental binding to the Jurkat cells in a dose-dependent manner, while no specific attachment was observed to 2PK3 cells in FIG. 4 and FIG. 10. The data demonstrates that anti-CD3ε peptide tetramers have specific affinity toward CD3ε-expressing Jurkat cells, and the affinity ($K_d$) is in the range of 100 μM.

Figure 5:
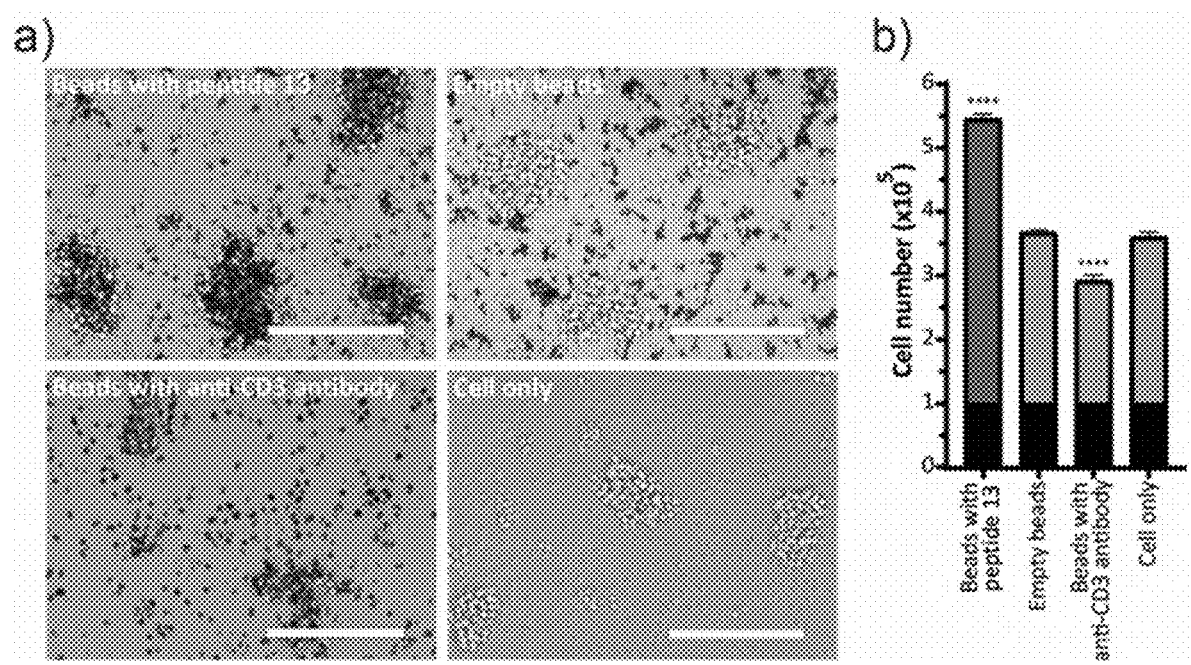
FIG. 5 displays images and a graphical representation of a) beads and Jurkat cells interaction after 24 hours: Interaction between the anti-CD3ε peptide beads to the Jurkat cells makes cells to form clumps around the beads while empty beads (control) don't result in clump formation. Anti-CD3 antibody beads showed a much tighter interaction while preventing cell proliferation. b) Viable cell numbers after 48 hours of incubation showed that beads with anti-CD3ε peptide 13 can enhance Jurkat cells proliferation while empty beads (control) doesn't show any effect on cell proliferation and anti-CD3 antibody beads showed a decrease in viable cell number, which can suggest that these beads might be involved in activation-induced apoptosis. The results are presented as means±SD, n=3, **** indicates $p<0.0001$. Scale bars represents 200 µm.
Figure 9:
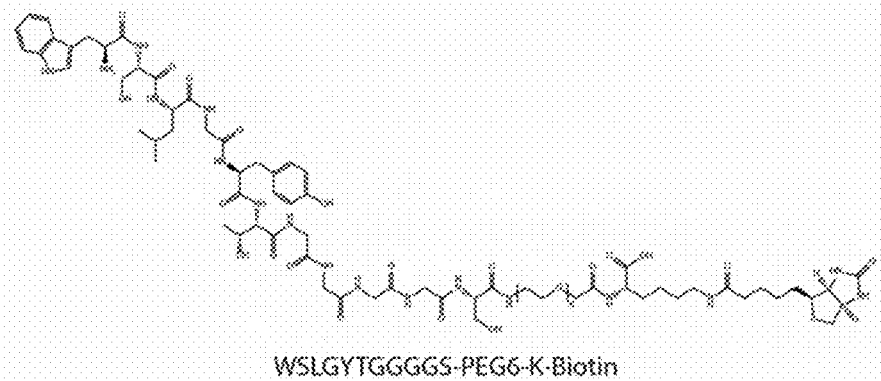
FIG. 9 is a set of schematics showing the chemical structure of synthesized anti-CD3ε peptides including anti-CD3ε peptide 13 in the form of (a) peptide tetramers, and (b) peptide beads.
Figure 9:
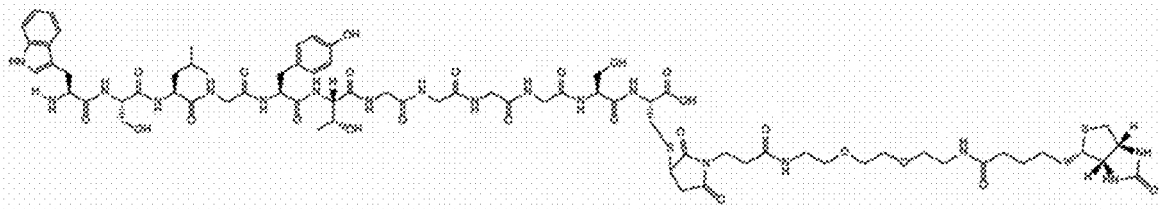
Figure 10:
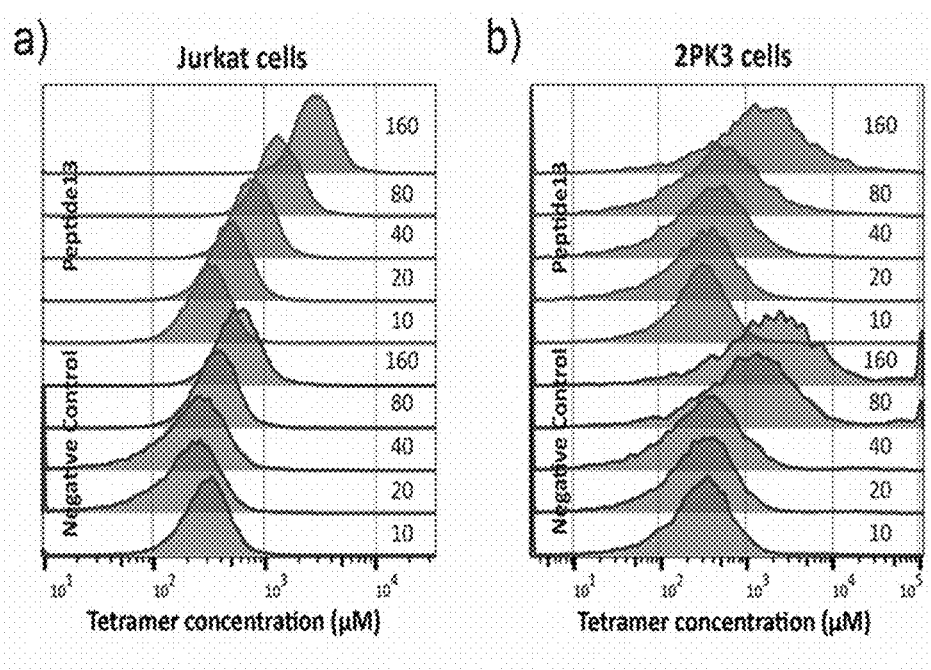
FIG. 10 displays flow cytometry histograms of anti-CD3ε peptide 13 tetramers on (a) Jurkat and (b) 2PK3 cells.
Figure 11:
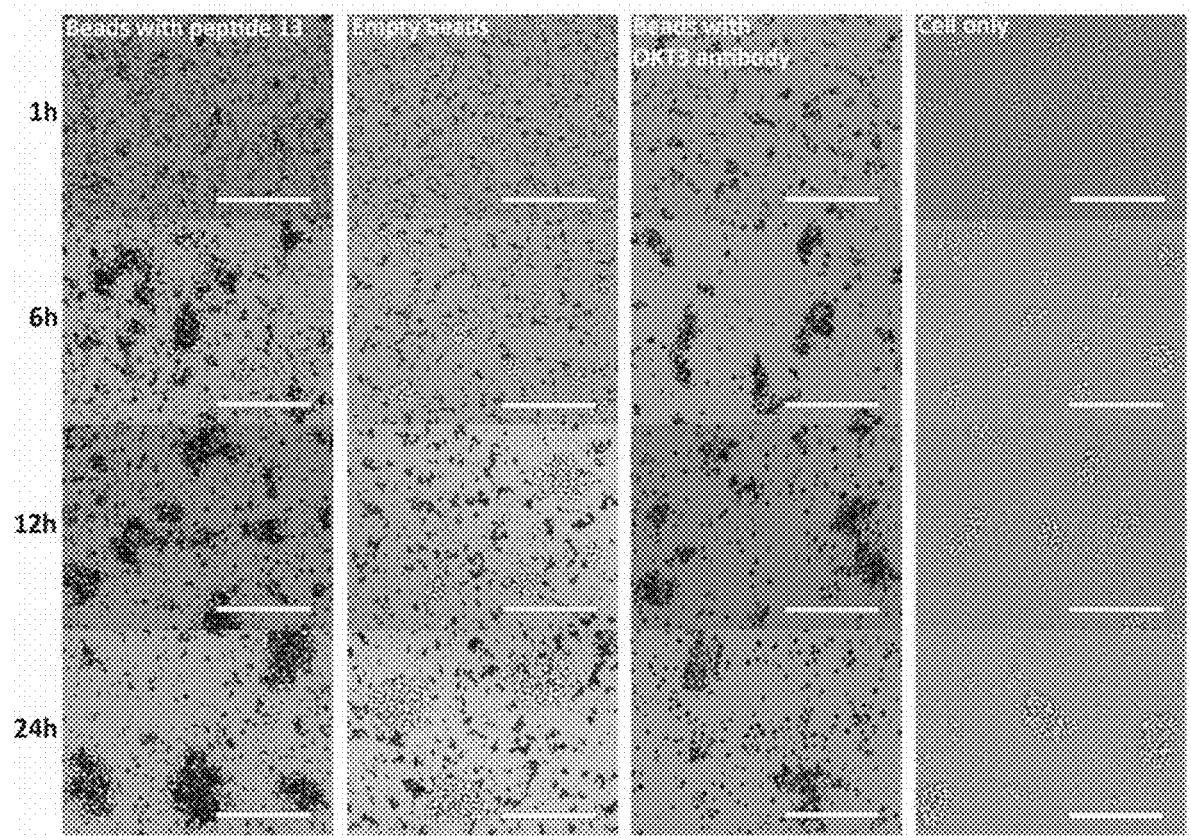
FIG. 11 shows optical microscope images of Jurkat cells and microbeads coated with indicated reagents and disclosed anti-CD3ε peptides over time. Scale bar represents 200 µm.
Figure 12:
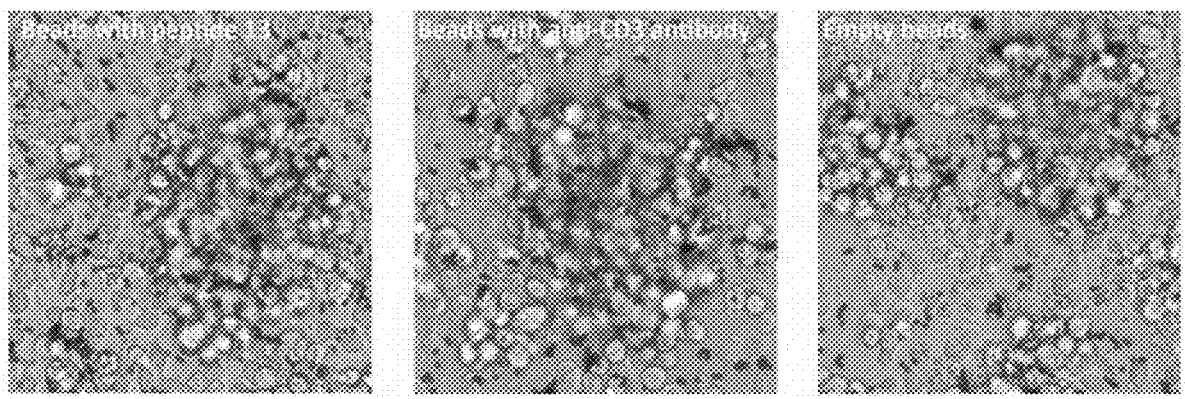
FIG. 12 shows optical microscope images of 2PK3 cells and microbeads coated with the indicated reagents and disclosed anti-CD3ε peptides at 24 hours.

2.6 Interaction Between Microbeads Coated with Peptide 13 and Jurkat Cells: To investigate the interaction of surface-conjugated anti-CD3ε peptide 13 and Jurkat cells, microbeads (M-280 streptavidin Dynabeads) coated with biotinylated anti-CD3ε peptide 13 (WSLGYTGGGGSC [SEQ ID NO: 32]-maleimide-PEG2-biotin) were prepared, as shown in FIG. 9 panel b. The interactions between Jurkat cells and the microbeads coated with the anti-CD3ε peptide 13 at ratio of 50 beads:1 cell were monitored, using optical microscopy over time for up to 24 hours, as shown in FIG. 11. Jurkat cells grew forming clumps (aggregates) and the clumps increased in size over time, as shown in FIG. 11. During this growth of Jurkat cells, the microbeads coated with anti-CD3ε peptide 13 quickly associated with Jurkat cells as early as 1 hour, and densely intercalated in the growing hybrid clumps of cells and microbeads, as shown in FIG. 5 and FIG. 11. In contrast, the empty microbeads (unmodified streptavidin microbeads) did not show any significant association with Jurkat cells and largely excluded from clumps of Jurkat cells. Meanwhile, microbeads coated with anti-CD3 antibody (OKT3) demonstrated similar association behaviors to microbeads coated with anti-CD3ε peptide 13. Possibly due to the stronger affinity, OKT3 microbeads bound to Jurkat cells much tighter than anti-CD3ε peptide microbeads, which left almost no microbeads free from association with Jurkat cells. It is worth noting that this specific association of microbeads coated with anti-CD3ε peptide 13 and OKT3 was not present when the same set of microbeads were incubated with 2PK3 cells, as shown in FIG. 12.

Figure 6:
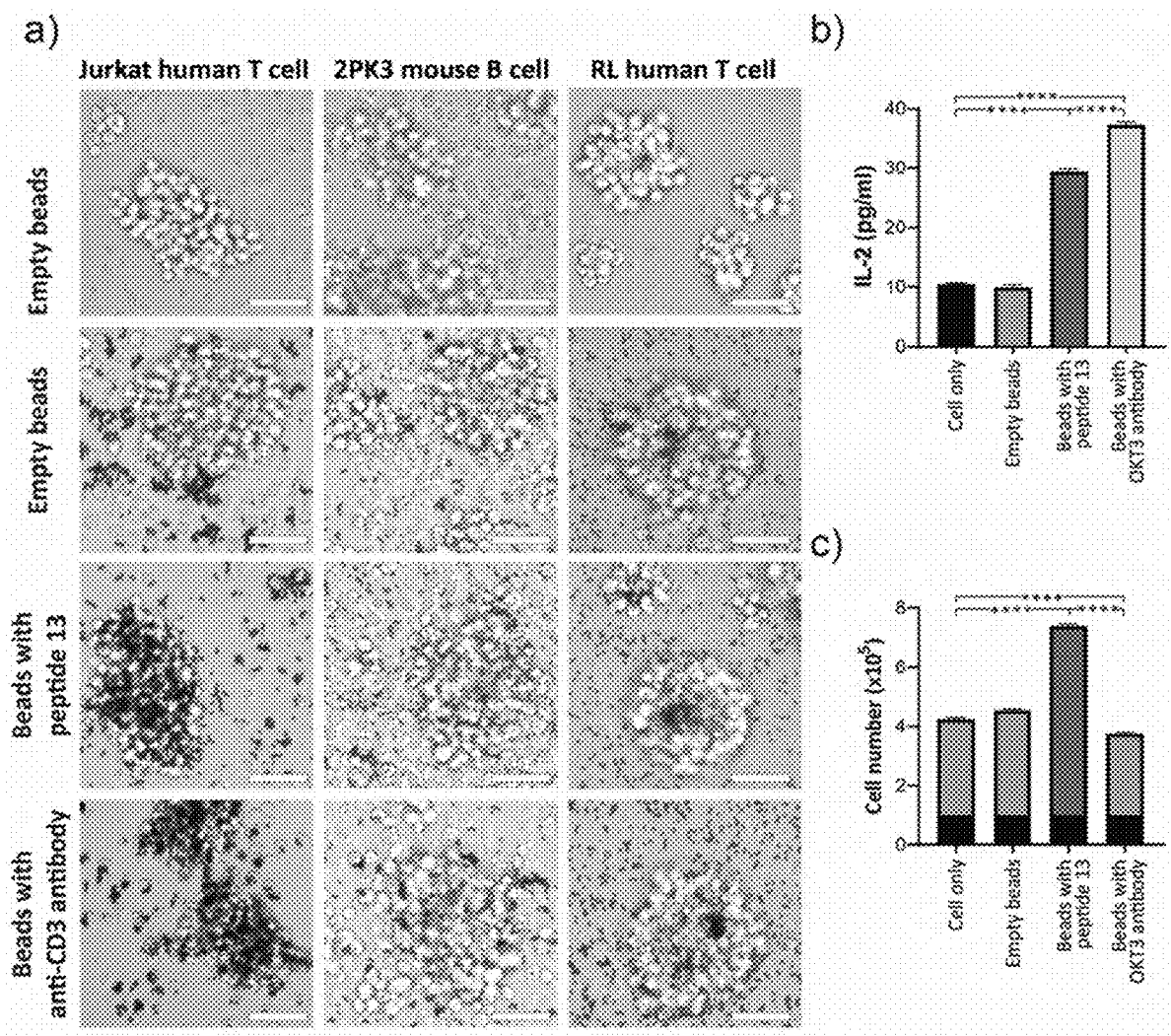
FIG. 6 shows images and graphical representations of specific interactions between the Jurkat cells and the microbeads coated with anti-CD3ε peptide 13 and the resulting biological effects, i.e. enhancement in IL2 secretion and increase in cell number (proliferation). (a) Optical microscope images showing the associations between the Jurkat cells and the indicated microbeads after incubation for 24 hours: Jurkat cells grow in clumps and appear in lighter contrasts; Darker contrasts originate from the microbeads. Scale bars represent 50 mm. (b) The levels of IL-2 secretion measured by ELISA. The supernatants were harvested after 20 hours of incubation of Jurkat cells in the corresponding conditions. (c) The number of viable cells counted after 48 hours of incubation in the corresponding conditions. The results are presented as means SD, n=3. Statistical significances from ordinary one-way ANOVA followed by Dunnett's multiple comparisons test comparing to cell only sample, are represented as ****($p<0.0001$).

As shown in FIG. 5, the growth of Jurkat cells and their clumps were the most robust with the anti-CD3ε peptide microbeads and the least with the OKT3 microbeads. The quantification of Jurkat cell numbers using a hemocytometer confirmed this observation under the microscope, as shown in FIG. 6. During 48 hours of culture, Jurkat cells incubated with the anti-CD3ε peptide microbeads expanded 4.5±0.07 times, while Jurkat cells incubated with empty beads or no beads expanded 2.7±0.04 or 2.6±0.07 times, respectively.

Again, the Jurkat cells with OKT3 microbeads expanded the least, only 1.9±0.09 times compared to the initial population.

Figure 13:
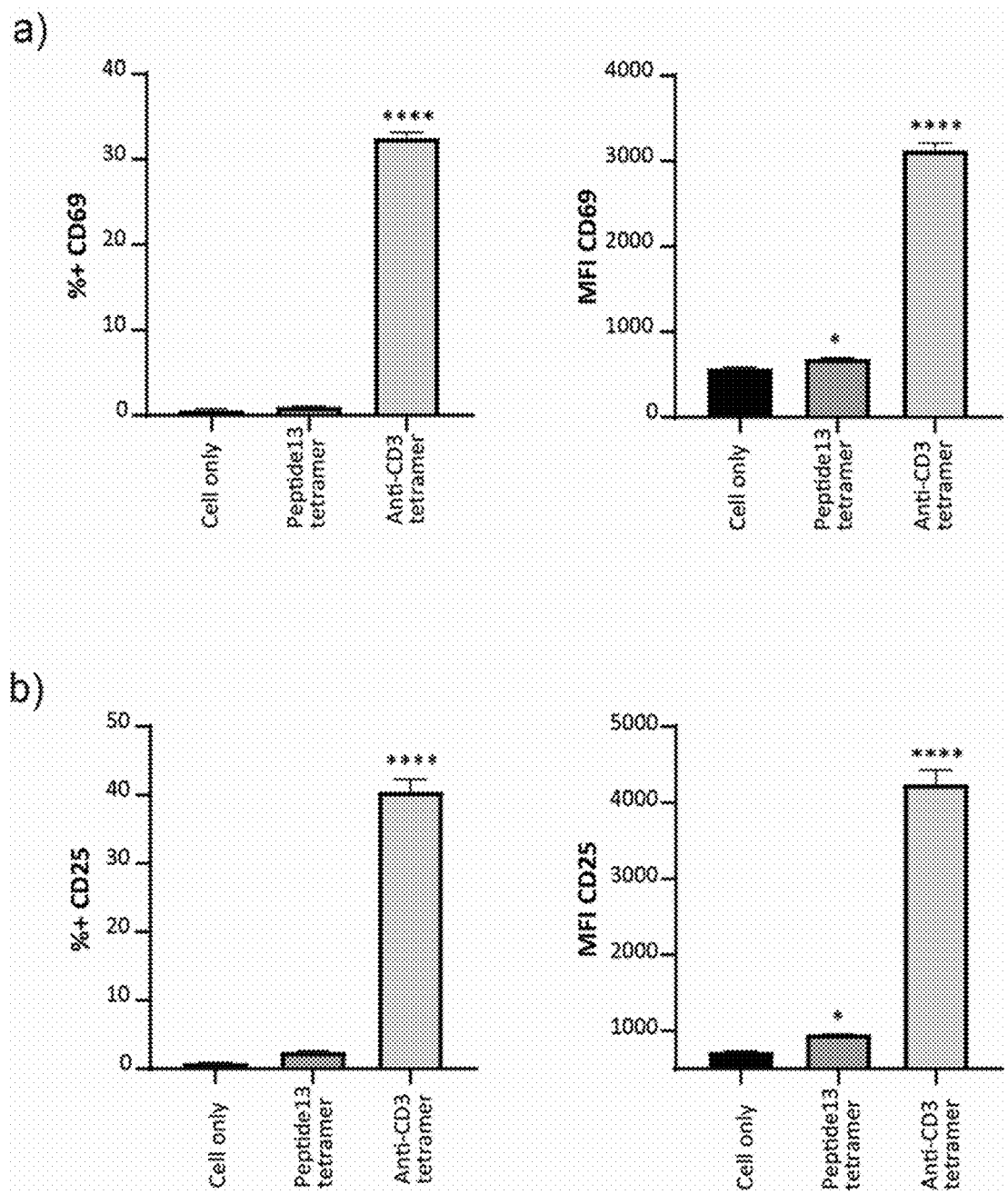
FIG. 13 shows expression of a) CD25 and b) CD69, T cell activation markers on Jurkat cells after incubation for 12 hours.

In order to examine if this difference in Jurkat cell expansion is a result of T cell activation, the expression level of CD25 and CD69 at 24 hours was examined, as shown in FIG. 13. Interestingly, the anti-CD3ε peptide microbeads did not upregulate either activation markers, while OKT3 microbeads induced significant upregulation of both CD25 and CD69.

Altogether, microbeads coated with anti-CD3ε peptide 13 can specifically associate with Jurkat cells and enhanced Jurkat cells proliferation, even if the activation markers CD25 and CD69 were not upregulated by such interactions. Stronger interactions between microbeads coated with OKT3 antibody and Jurkat cells induced upregulations of both activation markers, which ironically caused a reduction in Jurkat cell proliferation potentially due to the activation-induced apoptosis.

Figure 7:
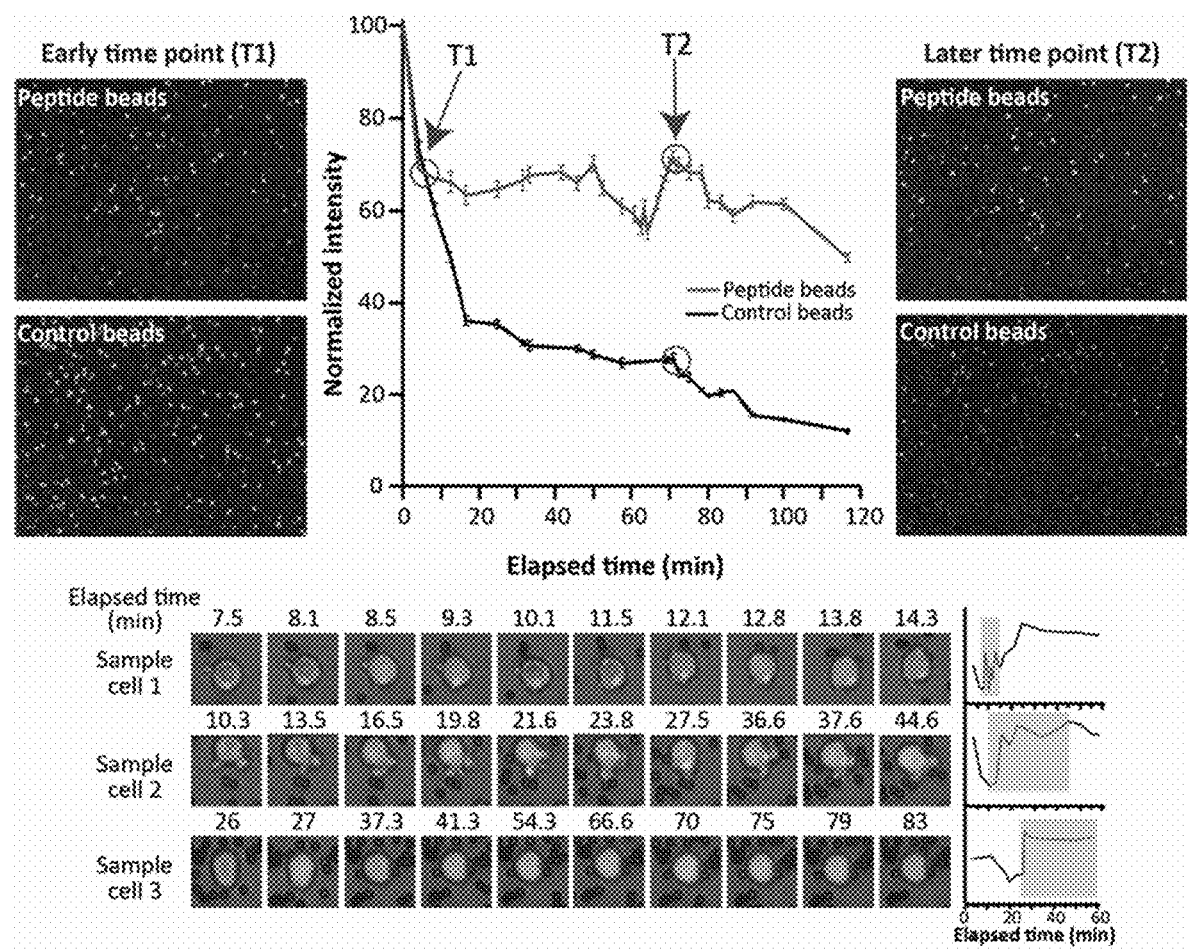
FIG. 7 displays images and graphical representations of calcium signaling of Jurkat cells triggered by the microbeads coated with anti-CD3ε peptide 13. The intensities of Fluo-4 ($Ca^{2+}$ indicator dye) from all Jurkat cells within the region of interest (575 µm by 425 µm) were averaged and normalized to the initial values, and plotted over time (grey line: peptide 13 beads, black line: empty streptavidin beads). The snapshots of Fluo-4 channel were taken at T1 and T2 indicated in the graph. The snapshots of three example cells that interact with anti-CD3ε peptide 13 microbeads were laid out for the corresponding elapsed time on top of each images. The individual Jurkat cells show their unique calcium flux profiles in graphs where the Fluo-4 intensities were plotted against the elapsed time. The periods corresponding to the snapshot images are indicated in grey shading in the right-side graphs.

2.7 Calcium Signalling: As the anti-CD3ε peptide 13 conjugated on the surface of microbeads did not significantly upregulate the early (CD69) and mid-term (CD25) activation markers on Jurkat cells by 24 hours, it was decided to examine more carefully if the anti-CD3ε peptide 13 can induce the TCR signaling at all. Among the main TCR signaling pathways such as MAPK, NF-κB, and calcium, the calcium signaling pathway has been shown to be the most sensitively responding to weak antigen stimulations. Following TCR/CD3 stimulation, the intracellular $Ca^{2+}$ increases due to calcium influx, whose onset time, duration, and the magnitude of the peak are directly proportional to the affinity of the antigenic pMHC. The transcription factor NFAT is well known to be calcium-sensitive and to contribute to T cell activation via production of interleukin-2 and other pro-survival factors. So, in order to monitor the calcium flux induced by the TCR/CD3 stimulation, the incubation of fluo-4 ($Ca^{2+}$ indicator dye)-loaded Jurkat cells and microbeads (5 beads:1 cell) was monitored in situ for 2 hours by a time-lapse microscopy on top of the onstage incubator maintaining 37° C. and 5% $CO_2$, as shown in FIG. 7. Both fluorescence and bright field images were taken every 10 seconds. When the Jurkat cells were incubated with empty beads, the average fluorescent intensity of the cells continuously decreased over time due to the photobleaching of Fluo-4 dye to reach 15% of its initial intensity at 2 hour point of time. However, the average fluorescent intensity of the Jurkat cells incubated with the anti-CD3ε peptide 13 microbeads sustained its value much higher than the control group for the entire 2-hour observation period (above 50% of initial intensity). The snapshots of the fluorescence channel taken for the collective population of Jurkat cells at T1 (−5 min) and T2 (−75 min) demonstrated that many Jurkat cells in the group with anti-CD3ε peptide 13 microbeads remained highly fluorescent at T2, while most of the Jurkat cells with empty control microbeads lost their fluorescent signals at T2 compared to T1. The collective fluorescence intensity is well supported by calcium flux patterns of the individual Jurkat cells recorded at a higher resolution. While there were no cells with calcium flux in the control group, the Jurkat cells interacting with anti-CD3ε peptide 13 microbeads showed active and lasting calcium fluxes. The overlay images of bright field and fluorescence channels for three sample Jurkat cells demonstrate that the individual Jurkat cells maintain active on-and-off interactions with anti-CD3ε peptide 13 microbeads at different points of time, when the Fluor-4 fluorescence signals increase and sustain, as shown in FIG. 7. It was very intriguing to observe the phenotypically similar behaviors of cytotoxic T lymphocytes (CTLs) from the Jurkat cells activated by interactions with microbeads with anti-CD3ε peptide 13. The killings of target cells by CTLs which elicit strong calcium signaling with concomitant tethering and engagement actions are followed by remaining committed to their initial dead target cells for hours, which might be related to the spatiotemporal coordination of CTL effector functions. Similarly, the Jurkat cells initially interacted with the anti-CD3ε peptide microbeads via active probing and tethering, but after the initiation of sustained calcium signaling, many of them became still, with a circular shape. The same behaviors were not observed from the Jurkat cells with empty beads.

Altogether, the anti-CD3ε peptide 13 conjugated to the microbeads can induce the proximal TCR signaling events that induce TCR signal transduction via calcium pathway. This novel microbead coated with anti-CD3ε peptide 13 presents its unique capability to universally induce a hierarchically specific TCR signaling without dependency on the affinity between TCR and pMHC.

2.8 Summary: Herein, novel anti-CD3ε peptide sequences are reported that have been selected against the human CD3ε via biopanning of a phage-display peptide library. The selected anti-CD3ε peptides' binding poses are predicted on the surface of CD3ε by molecular docking, from which it has been confirmed that some of the most energetically favorable poses enable the anti-CD3ε peptides to bind to the "exposed" site of physiologically expressed CD3ε in complex with TCR and other CD3 chains. Indeed, the synthetic anti-CD3ε peptides FWSSPQM and WSLGYTG in their tetramer forms can bind specifically to Jurkat cells in a dose-dependent manner. It was demonstrated that the microbeads decorated with the anti-CD3ε peptide 13 can specifically associate with Jurkat cells but not 2PK3 cells, which enhanced the proliferation of Jurkat cells. The anti-CD3ε peptide-coated microbeads successfully induce a proximal TCR signaling events exhibited by active and sustained calcium fluxes. Therefore, these anti-CD3ε peptide ligands with a very specific affinities against human CD3ε has unique properties to mimic some interactions between TCR and pMHC, and thus may be utilized in various applications using T lymphocytes such as T cell immunotherapies.

Example 2

1.1 Phage Clones Presenting Peptides Against CD3ε Were Enriched and Identified by Subtractive Biopanning and Bioinformatics Tools: The phage clones were first selected that can bind specifically to the recombinant human CD3ε protein through biopanning experiments using 7-mer peptide phage library. As an example, in one experiment ($2^{nd}$ experiment), after each round of panning, the phage recovery ratio was measured, and it showed an exponential increase up to the 5th round, as shown in FIG. 1, which indicates that the phage clones capable of specifically binding to CD3ε were significantly enriched at every round of biopanning. Twenty out of about 100 plaques (colonies from tittered Xgal-IPTG plates) were randomly selected, and the ssDNA from each clone was purified after 3rd and 5th rounds. Twelve and three unique peptide sequences were identified from rounds 3 and 5, respectively. As two clones identified after 5th round were pre-identified from the 3rd round, a total of 13 unique clones were identified.

Before proceeding to further analyses, all anti-CD3ε peptide sequences were examined to verify if any of the discovered sequences either had been previously reported or had a potential to be false positives. Some of the most widely used bioinformatics tools were employed, namely SmartBlast search tool, SAR-OTUP suite, and pepATTRACT web server.

First, it was determined whether any of these 13 sequences had been identified or reported in other literatures using SmartBLAST database. None of the 13 anti-CD3ε peptide sequences yielded matching queries. Then, all anti-CD3ε peptides were analyzed using SAROTUP 3.1 (Scanner And Reporter Of Target-Unrelated Peptides) web server for identification of potential target-unrelated peptides (TUPs). TUPScan in SAROTUP server, which is designed to check if the tested peptides match any known TUP motifs, identified the clone 6 as a confirmed plastic (polystyrene) binder. In a more detailed analysis using individual modules of SAROTUP, clone 14 and 24 were also screened as potential polystyrene binders from the PSBinder module. Additionally, clone 15 was predicted as a potential clone that propagates faster than others within the PhD-7 phage display peptide library, according to the PhD7Faster algorithm. The SABinder module64 confirmed that none of the 13 anti-CD3ε peptides have significant potential to bind to streptavidin. Lastly, rapid molecular docking experiments were performed using pepATTRACT Web server to study the strength of the peptide-protein interactions by calculating binding energy levels. As anti-CD3ε peptide 16 showed a binding energy level that is almost equivalent to random sequences, it was decided to exclude this clone from further analyses.

Out of 13 selected phage cones from the $2^{nd}$ experiment, it was decided to exclude total 5 clones (4 identified as TUPs and 1 potential random selection). All remaining 8 clones (clone 13, 17, 18, 19, 20, 21, 22, and 23) with minimal risk of being a false positive were studied in further experiments. Based on the corresponding frequency of each sequence, phage clone 13 displaying anti-CD3ε peptide WSLGYTG demonstrated a particularly dominant enrichment.

1.2 Phage Clone 13 Showed a Dominant Binding Against Recombinant CD3ε on Microbeads: As the first step to verifying the specific binding capability of all eight candidate phage clones, the binding behaviors of each phage clone to the target protein, human CD3ε decorated on the surface of magnetic beads was examined using flow cytometry. As it is possible that the most enriched clone may not be the actual best binder to the target, similar binding assays are often carried out. Additionally, as the recombinant CD3ε employed in the biopanning experiment had a large Fc tag (around 25 kDa), a biotinylated CD3ε was employed at the C-terminus instead to decorate the streptavidin-coated microbeads, to further eliminate the chance of selecting Fc-binding false positives.

We claim:

1. A ligand for binding human cluster of differentiation 3 epsilon (CD3ε) represented by SEQ ID NO: 13.

2. A ligand for binding human cluster of differentiation 3 epsilon (CD3ε) having the formula: SEQ ID NO:31-PEG6-lysine-biotin.

3. A ligand for binding human cluster of differentiation 3 epsilon (CD3ε) having the formula: SEQ ID NO: 32-maleimide-PEG2-biotin.

4. A ligand for binding human cluster of differentiation 3 epsilon (CD3ε) represented by SEQ ID NO: 13 and coupled to a labeling molecule by an attachment group of the ligand.

5. The ligand of claim 4, wherein the labeling molecule is a fluorescent label, enzyme label, chromogenic label, luminescence label, radiation label, magnetic label, metal complex, metal, or colloidal gold.

* * * * *

SEQUENCE LISTING

```
<160> NUMBER OF SEQ ID NOS: 32

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 1

<400> SEQUENCE: 1

Glu Val Phe Gln Thr Pro Ile
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 2

<400> SEQUENCE: 2

His Pro Ser Thr Trp His Lys
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 3

<400> SEQUENCE: 3

His Ala Leu Pro Asn Tyr Lys
1               5

<210> SEQ ID NO 4
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      Anti-CD3E Peptide 4

<400> SEQUENCE: 4

Gln Ala Ser Ser Leu Pro Trp
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 5

<400> SEQUENCE: 5

Ser Met Leu Ser Ser Ile Phe
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 6

<400> SEQUENCE: 6

Glu Pro Val Arg Leu Gln Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 7

<400> SEQUENCE: 7

Phe Gln Ser Lys Ser Ser Ile
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 8

<400> SEQUENCE: 8

Ser Pro Ser Arg His Ile Asn
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 9

<400> SEQUENCE: 9

Thr Trp Thr Leu Ala Arg Pro
```

```
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide
      10

<400> SEQUENCE: 10

Ser Leu Gln Arg Met Thr Trp
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 11

<400> SEQUENCE: 11

Phe Trp Ser Ser Pro Gln Met
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 12

<400> SEQUENCE: 12

Ser Tyr Ala Pro Pro Thr Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 13

<400> SEQUENCE: 13

Trp Ser Leu Gly Tyr Thr Gly
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 14

<400> SEQUENCE: 14

Gly Thr Ile Tyr Trp Asn Ser
1               5

<210> SEQ ID NO 15
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      Anti-CD3E Peptide 15

<400> SEQUENCE: 15

Ser Pro Leu Ser Pro Arg Tyr
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 16

<400> SEQUENCE: 16

Glu Thr Gly Ile Thr Arg Gln
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 17

<400> SEQUENCE: 17

Trp Ile Phe Thr Pro Leu Gly
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 18

<400> SEQUENCE: 18

Arg Asn Ser Trp Pro Val Trp
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 19

<400> SEQUENCE: 19

Gly Ser Ser Gly Lys Pro Gly
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 20

<400> SEQUENCE: 20

Arg Gly Thr Gly His Tyr Trp
1               5
```

```
<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 21

<400> SEQUENCE: 21

Trp Trp Ser Thr His Asp Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 22

<400> SEQUENCE: 22

Arg Asn Met Arg Gly Tyr Gly
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 23

<400> SEQUENCE: 23

Trp Thr Ala Arg Pro Thr Gly
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 24

<400> SEQUENCE: 24

Gly Ser Trp Thr Thr Gly Gln
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 25

<400> SEQUENCE: 25

Tyr Asn His Thr Met Met Tyr
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 26

<400> SEQUENCE: 26
```

```
<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 27

<400> SEQUENCE: 27

Trp Met Ser Ser Pro Thr Gly
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 28

<400> SEQUENCE: 28

Trp Ile Ser Ser Pro Thr Gly
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD3E Peptide 29

<400> SEQUENCE: 29

Thr Trp Ser Ser Pro Thr Gly
1               5

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      Anti-CD3E Peptide 30

<400> SEQUENCE: 30

Phe Trp Ser Ser Pro Gln Met Gly Gly Gly Ser
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      Anti-CD3E Peptide 31

<400> SEQUENCE: 31

Trp Ser Leu Gly Tyr Thr Gly Gly Gly Gly Ser
1               5                   10

<210> SEQ ID NO 32
<211> LENGTH: 12
<212> TYPE: PRT
<213> ORGANISM: Artificial Sequence
```

(Preceding context before SEQ ID NO 27:)
```
Trp Trp Ser Ser Pro Thr Gly
1               5
```

```
<220> FEATURE:
<223> OTHER INFORMATION: Description of Artificial Sequence: Synthetic
      Anti-CD3E Peptide 32

<400> SEQUENCE: 32

Trp Ser Leu Gly Tyr Thr Gly Gly Gly Ser Cys
1               5                   10
```